US012737881B2

(12) United States Patent
Tong

(10) Patent No.: US 12,737,881 B2
(45) Date of Patent: Sep. 15, 2026

(54) SYSTEMS AND METHODS FOR SIGNAL PROCESSING

(71) Applicant: SHANGHAI UNITED IMAGING HEALTHCARE CO., LTD., Shanghai (CN)

(72) Inventor: Li Tong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 369 days.

(21) Appl. No.: 18/365,977

(22) Filed: Aug. 5, 2023

(65) Prior Publication Data

US 2024/0046469 A1 Feb. 8, 2024

(30) Foreign Application Priority Data

Aug. 5, 2022 (CN) ......................... 202210937865.5
Aug. 5, 2022 (CN) ......................... 202210939666.8
Aug. 29, 2022 (CN) ......................... 202211041673.2

(51) Int. Cl.

| | |
|---|---|
| ***G06V 10/774*** | (2022.01) |
| ***G01R 33/56*** | (2006.01) |
| ***G06T 7/00*** | (2017.01) |
| ***G06V 10/94*** | (2022.01) |
| ***G16H 30/20*** | (2018.01) |
| ***G16H 40/67*** | (2018.01) |

(52) U.S. Cl.

CPC ........ *G06T 7/0012* (2013.01); *G01R 33/5608* (2013.01); *G06V 10/774* (2022.01);
(Continued)

(58) Field of Classification Search

CPC ......... G06T 7/0012; G06T 2207/10088; G06T 2207/20081; G06T 2207/30004;
(Continued)

(56) References Cited

U.S. PATENT DOCUMENTS 10,716,533 B2 * 7/2020 Kahya .................... G16H 40/67
11,527,313 B1 * 12/2022 Talvola ............. G06Q 30/0201
(Continued)

FOREIGN PATENT DOCUMENTS

CN 112509074 A 3/2021
CN 112686385 A 4/2021
(Continued)

OTHER PUBLICATIONS

Su, Jiasheng et al., A CNN Based Software Gradiometer for Electromagnetic Background Noise Reduction in Low Field Mri Applications, IEEE Transactions on Medical Imaging, 2020, 10 pages.
(Continued)

*Primary Examiner* — Andrew W Bee
*Assistant Examiner* — D J Dhooge
(74) *Attorney, Agent, or Firm* — METIS IP LLC

(57) ABSTRACT

The present disclosure provides methods and systems for federated learning. The systems include a central server and client devices communicatively connected with the central server. The central server may be configured to maintain a global prediction model for signal prediction, and each of the client devices is configured to maintain a local prediction model for signal prediction corresponding to at least one medical device. The client devices include one or more target client devices.

20 Claims, 14 Drawing Sheets

(52) U.S. Cl.
CPC ............. *G06V 10/95* (2022.01); *G16H 30/20* (2018.01); *G16H 40/67* (2018.01); *G06T 2207/10088* (2013.01); *G06T 2207/20081* (2013.01); *G06T 2207/30004* (2013.01); *G06T 2207/30168* (2013.01); *G06V 2201/03* (2022.01)

(58) Field of Classification Search
CPC . G06T 2207/30168; G06T 2207/20084; G06T 5/60; G06T 5/70; G01R 33/5608; G01R 33/5659; G06V 10/774; G06V 10/95; G06V 2201/03; G06V 10/82; G06V 10/98; G16H 30/20; G16H 40/67; G16H 50/20; G06F 18/2413; G06F 18/2433
See application file for complete search history.

(56) References Cited

U.S. PATENT DOCUMENTS

| | | | | |
|---|---|---|---|---|
| 2018/0189457 | A1* | 7/2018 | Plummer | G16H 50/70 |
| 2018/0365531 | A1* | 12/2018 | Gopalan | G06F 18/24147 |
| 2020/0294401 | A1 | 9/2020 | Kerecsen | |
| 2023/0289591 | A1* | 9/2023 | Cyras | G06N 3/0499 |

FOREIGN PATENT DOCUMENTS

| | | | | |
|---|---|---|---|---|
| CN | 113627085 A | | 11/2021 | |
| CN | 113655424 A | | 11/2021 | |
| CN | 113848520 A | | 12/2021 | |
| CN | 114912022 A | | 8/2022 | |
| WO | WO-2020205649 A9 | * | 5/2021 | G16B 40/20 |
| WO | 2022116429 A1 | | 6/2022 | |

OTHER PUBLICATIONS

Liu, Yilong et al., A Low-cost and Shielding-free Ultra-low-field Brain MRI Scanner, Nature Communications, 2021, 14 pages.

First Office Action in Chinese Application No. 202211041673.2 mailed on Apr. 28, 2026, 34 pages.

* cited by examiner

1100

SYSTEMS AND METHODS FOR SIGNAL PROCESSING

CROSS-REFERENCE TO RELATED APPLICATIONS

This application claims priority to Chinese Patent Application No. 202211041673.2, filed on Aug. 29, 2022, Chinese Patent Application No. 202210939666.8, filed on Aug. 5, 2022, and Chinese Patent Application No. 202210937865.5, filed on Aug. 5, 2022, the contents of each of which are incorporated herein by reference.

TECHNICAL FIELD

The present disclosure generally relates to signal processing, and more particularly, relates to systems and methods for interference signal reduction.

BACKGROUND

Medical imaging techniques (e.g., a magnetic resonance (MR) technique, a computed tomography (CT) technique, a positron emission tomography (PET) technique, etc.) are used to obtain imaging data (e.g., imaging signals) of a target subject. However, interference signals can be acquired during the acquisition of the imaging data, which reduces the accuracy and image quality of image(s) of the target subject generated based on the imaging data.

Therefore, it is desirable to provide systems and methods for signal processing, which can reduce the effect of the interference signals acquired during the acquisition of the imaging data, thereby improving the accuracy and image quality of the generated image(s).

SUMMARY

In an aspect of the present disclosure, a system is provided. The system may include a central server and client devices. The central server may be configured to maintain a global prediction model for signal prediction, and the client devices may be communicatively connected with the central server. Each of the client devices may be configured to maintain a local prediction model for signal prediction corresponding to at least one medical device. The client devices may include one or more target client devices. Each of the one or more target client devices may be configured to receive new sample data corresponding to the target client device, generate an updated local prediction model by updating its local prediction model using the new sample data, and transmit first model information relating to the updated local prediction model to the central server, and the central server may be configured to generate an updated global prediction model by updating the global prediction model based on the first model information received from the one or more target client devices, and transmit second model information relating to the updated global prediction model to each of the client devices such that the client devices can update their respective local prediction models based on the second model information.

In some embodiments, for each of the one or more target client devices, the new sample data may include at least one of first sample interference signals and second sample interference signals, the first sample interference signals may be collected by at least one receiver coil of the at least one medical device corresponding to the target client device, and the second sample interference signals may be collected by at least one interference signal acquisition device corresponding to the target client device.

In some embodiments, to transmit first model information may relate to the updated local prediction model to the central server, each of the one or more target client devices may be further configured to: generate encrypted first model information by encrypting the first model information; and transmit the encrypted first model information to the central server.

In some embodiments, to generate an updated local prediction model by updating its local prediction model using the new sample data, each of the one or more target client devices may be further configured to: determine whether the local prediction model of the target client device needs to be trained based on the new sample data; and in response to determining that the local prediction model of the target client device needs to be trained based on the new sample data, generate the updated local prediction model by updating its local prediction model using the new sample data.

In some embodiments, each of the client devices may be further configured to maintain a second local prediction model, and in response to determining that the local prediction model of the target client device does not need to be trained, the target client device may be further configured to: generate an updated second local prediction model by updating the second local prediction model using the new sample data.

In some embodiments, the new sample data may include a first portion of the new sample data and a second portion of the new sample data, the first portion of the new sample data may relate to general information of the at least one medical device corresponding to the target client device, the second portion of the new sample data may relate to special information of the at least one medical device corresponding to the target client device, the local prediction model of the target client device may be trained using the first portion of the new sample data, and the general information may include general signal interference. The second local prediction model of the client device may be trained using the second portion of the new sample data, and the special information may include at least one of signal interference relating to a location where the target client device is located and signal interference relating to a special device.

In some embodiments, the one or more target client devices may include a plurality of target client devices, and to generate an updated global prediction model by updating the global prediction model based on the first model information received from the one or more target client devices, the central server may be further configured to determine a weighting value corresponding to each of the plurality of target client devices; and generate the updated global prediction model by updating the global prediction model based on the first model information received from the plurality of target client devices and the weighting value corresponding to each of the plurality of target client devices.

In some embodiments, to determine a weighting value corresponding to each of the plurality of target client devices, the central server may be further configured to: for each of the plurality of target client devices, obtain a training condition of the local prediction model of the target client device, the training condition including at least one of a volume of the new sample data used in training the local prediction model and a prediction accuracy of the local prediction model; and determine the weighting value corresponding to each of the plurality of target client devices based on the training condition corresponding to each of the plurality of target client devices.

In some embodiments, each of the client devices may be further configured to: obtain initial signals collected by at least one receiver coil of the at least one medical device corresponding to the client device; generate unwanted interference signals based on the updated local prediction model and the initial signals; and determine target imaging signals based on the unwanted interference signals and the initial signals.

In some embodiments, the local prediction model may include a first prediction model for interference signal prediction, and each of the client devices may be further configured to: obtaining initial signals and first interference signals collected in a time window of a medical scan of a target subject when the target subject is in an excited state, the initial signals being collected by a receiver coil of the at least one medical device, and the first interference signals being collected by an interference signal acquisition device; determining feature information of the first interference signals; determining the first prediction model for interference signal prediction based on the feature information; and determining target imaging signals included in the initial signals based on the first prediction model and the first interference signals.

In some embodiments, the local prediction model may include a second prediction model, and each of the client devices may be further configured to: obtaining initial signals and interference signals collected in a time window of a medical scan of a target subject, the initial signals being collected by a receiver coil of the at least one medical device when the target subject is in an excited state, and the interference signals being collected by an interference signal acquisition device; determining target imaging signals included in the initial signals by processing the initial signals and the interference signals using the second prediction model, the second prediction model being a trained machine learning model; and generating a target MR image of the target subject based on the target imaging signals.

In another aspect of the present disclosure, a method for signal processing is provided. The method for signal processing may be implemented on a client device among client devices communicatively connected with a central server, wherein the central server is configured to maintain a global prediction model for signal prediction, the client device is configured to maintain a local prediction model for signal prediction corresponding to at least one medical device. The method may include obtain initial signals collected by at least one receiver coil of the at least one medical device corresponding to the client device; generate unwanted interference signals based on an updated local prediction model and the initial signals; and determine target imaging signals based on the unwanted interference signals and the initial signals. The updated local prediction model may be obtained by: updating the local prediction models based on second model information from the central server, wherein the client devices include one or more target client devices, each of the one or more target client devices is configured to receive new sample data corresponding to the target client device, generate an updated local prediction model corresponding to the target client device by updating its local prediction model using the new sample data, and transmit first model information relating to the updated local prediction model corresponding to the target client device to the central server, and the central server is configured to generate an updated global prediction model by updating the global prediction model based on first model information received from the one or more target client devices, and transmit the second model information relating to the updated global prediction model to each of the client devices.

In still another aspect of the present disclosure, a non-transitory computer readable medium is provided. The non-transitory computer readable medium may include executable instructions that, when executed by at least one processor, direct the at least one processor to perform a method. The method may include obtaining initial signals collected by at least one receiver coil of at least one medical device corresponding to a client device; generating unwanted interference signals based on an updated local prediction model and the initial signals; and determining target imaging signals based on the unwanted interference signals and the initial signals. The client device may be one of client devices communicatively connected with a central server, the central server may be configured to maintain a global prediction model for signal prediction, the client device may be configured to maintain a local prediction model for signal prediction corresponding to the at least one medical device, and the updated local prediction model may be obtained by: updating the local prediction models based on second model information from the central server, wherein the client devices include one or more target client devices, each of the one or more target client devices is configured to receive new sample data corresponding to the target client device, generate an updated local prediction model corresponding to the target client device by updating its local prediction model using the new sample data, and transmit first model information relating to the updated local prediction model corresponding to the target client device to the central server, and the central server is configured to generate an updated global prediction model by updating the global prediction model based on first model information received from the one or more target client devices, and transmit the second model information relating to the updated global prediction model to each of the client devices.

In yet another aspect of the present disclosure, a method for signal processing is provided. The method for signal processing may be implemented on a computing device having at least one processor and at least one storage device. The method may include obtaining initial signals and first interference signals collected in a time window of a magnetic resonance (MR) scan of a target subject when the target subject is in an excited state, the initial signals being collected by a receiver coil of a magnetic resonance imaging (MRI) device, and the first interference signals being collected by an interference signal acquisition device; determining feature information of the first interference signals; determining a first prediction model for interference signal prediction based on the feature information; and determining target imaging signals included in the initial signals based on the first prediction model and the first interference signals.

In some embodiments, the feature information of the first interference signals may include at least one of an interference degree or an interference type.

In some embodiments, the determining a first prediction model for interference signal prediction based on the feature information may include determining whether the first interference signals are abnormal based on the feature information; in response to determining that the first interference signals are not abnormal, determining a pre-trained prediction model as the first prediction model; or in response to determining that the first interference signals are abnormal, determining the first prediction model by updating the pre-trained prediction model.

In some embodiments, the updating the pre-trained prediction model may include obtaining second interference signals and third interference signals collected in a second time window of the MR scan of the target subject when the target subject is in an unexcited state, the second interference signals collected by the receiver coil of the MRI device, and the third interference signals being collected by the interference signal acquisition device; and updating the pre-trained prediction model based on the second interference signals and the third interference signals.

In some embodiments, the determining a first prediction model for interference signal prediction based on the feature information may include obtaining a plurality of pre-trained prediction models; obtaining a corresponding relationship between the plurality of pre-trained prediction models and reference feature information; and determining the first prediction model from the plurality of pre-trained prediction models based on the feature information and the corresponding relationship.

In some embodiments, the determining feature information of the first interference signals may include determining the feature information of the first interference signals using a feature discrimination model, the feature discrimination model being a trained machine learning model.

In some embodiments, the feature discrimination model may include a first feature discrimination model and a second feature discrimination model, wherein the first feature discrimination model is configured to determine an interference degree of the first interference signals, and the second feature discrimination model is configured to determine an interference type of the first interference signals.

In some embodiments, the method may further include determining unwanted interference signals included in the initial signals based on the first prediction model and the first interference signals; determining reference interference signals and reference imaging signals based on a second prediction model, the initial signals, and the first interference signals; determining a first difference between the reference interference signals and the unwanted interference signals and a second difference between the reference imaging signals and the target imaging signals; determining whether the first difference and the second difference satisfy a preset condition; and in response to determining that the first difference and the second difference satisfy the preset condition, updating the first prediction model.

In yet another aspect of the present disclosure, a method for image generation is provided. The method for image generation may be implemented on a computing device having at least one processor and at least one storage device. The method may include obtaining initial signals and interference signals collected in a time window of a magnetic resonance (MR) scan of a target subject, the initial signals being collected by a receiver coil of a magnetic resonance imaging (MRI) device when the target subject is in an excited state, and the interference signals being collected by an interference signal acquisition device; determining target imaging signals included in the initial signals by processing the initial signals and the interference signals using a prediction model, the prediction model being a trained machine learning model; and generating a target MR image of the target subject based on the target imaging signals.

In some embodiments, the prediction model may be determined by: obtaining training data including sample initial signals and sample interference signals; generating predicted imaging signals and predicted interference signals based on the training data and an initial prediction model; generating a reference output by processing the predicted imaging signals using a reference model; and determining the prediction model by updating the initial prediction model based on the reference output.

In some embodiments, the reference model may include a first discrimination model, the training data may further include pure imaging signals collected under an interference-free environment, and the reference output may include a first discrimination result relating to the pure imaging signals and the predicted imaging In some embodiments, the reference model may include a second discrimination model, the training data may further include pure interference signals collected by a sample receiver coil when the sample subject is in an unexcited state, and the reference output may include a second discrimination result relating to the pure interference signals and the predicted interference signals.

In some embodiments, the reference model may include a signal fusion model, the generating a reference output by processing the predicted imaging signals using a reference model may include: generating a signal fusion result by processing the predicted imaging signals and the predicted interference signals using the signal fusion model, and the updating the initial prediction model may include: updating the initial prediction model based on the signal fusion result and the initial signals.

In some embodiments, the reference model may include a third discrimination model, and the updating the initial prediction model may include: generating a third determination result based on the signal fusion result, the initial signals, and the third reference model; and updating the initial prediction model based on the third determination result.

In some embodiments, the reference model may be a pre-trained model.

In some embodiments, the reference model may be a model to be trained, and the determining the prediction model by updating the initial prediction model based on the reference output may include determining the prediction model by jointly updating the reference model and the initial prediction model based on the reference output.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
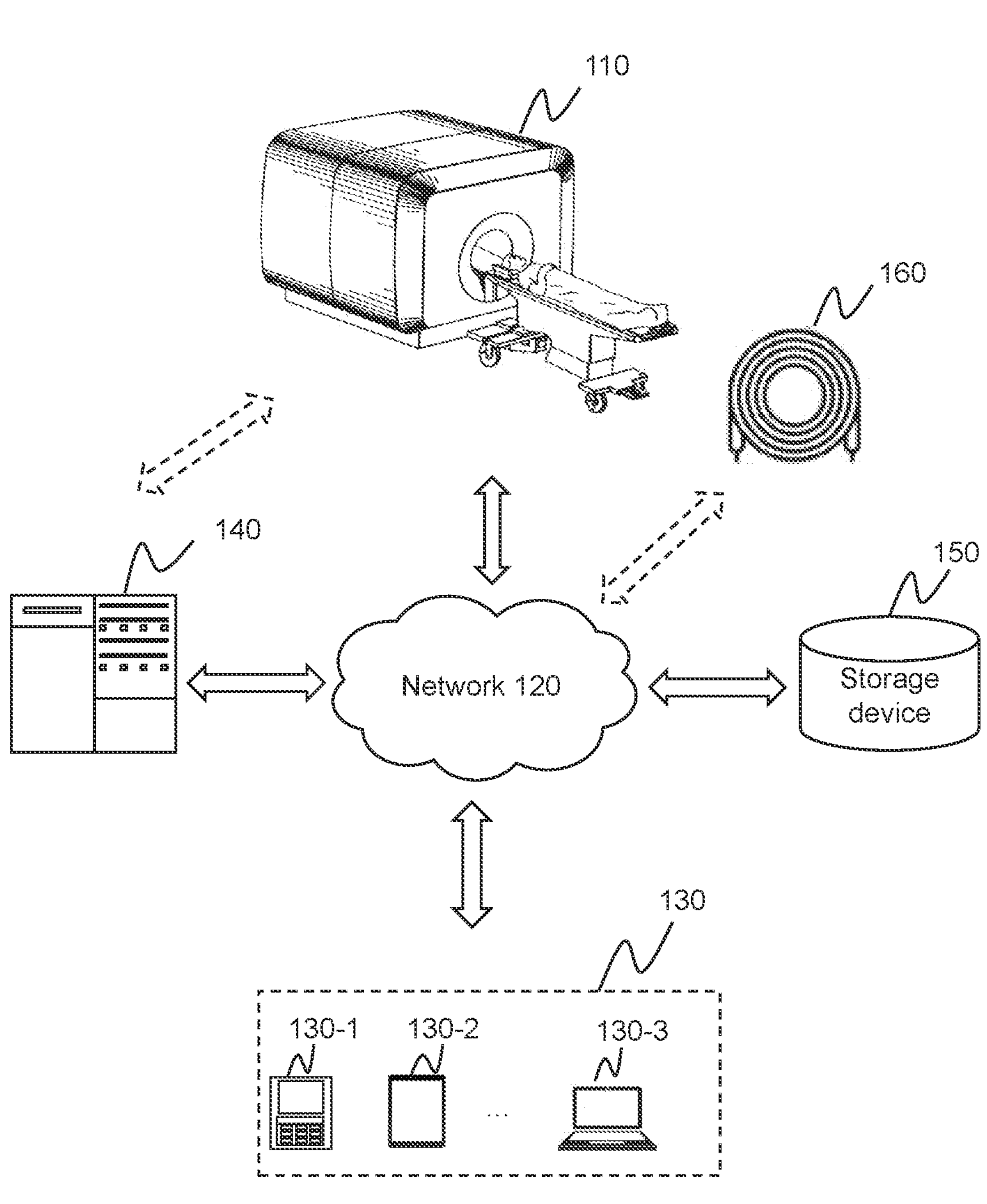
FIG. 1 is a schematic diagram illustrating an exemplary signal processing system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for non-invasive biomedical imaging/treatment, such as for disease diagnostic, disease therapy, or research purposes. In some embodiments, the systems may include an imaging system. The imaging system may include a single modality system and/or a multi-modality system. The term "modality" used herein broadly refers to an imaging or treatment method or technology that gathers, generates, processes, and/or analyzes imaging information of a subject or treatments the subject. The single modality system may include, for example, a magnetic resonance imaging (MRI) system, an ultrasound imaging system, an X-ray imaging system, a computed tomography (CT) system, an ultrasonography system, a positron emission tomography (PET) system, an optical coherence tomography (OCT) imaging system, an ultrasound (US) imaging system, an intravascular ultrasound (IVUS) imaging system, a near-infrared spectroscopy (NIRS) imaging system, or the like, or any combination thereof. The multi-modality system may include, for example, an X-ray imaging-magnetic resonance imaging (X-ray-MRI) system, a positron emission tomography-X-ray imaging (PET-X-ray) system, a single photon emission computed tomography-magnetic resonance imaging (SPECT-MRI) system, a positron emission tomography-computed tomography (PET-CT) system, a C-arm system, a positron emission tomography-magnetic resonance imaging (PET-MR) system, a digital subtraction angiography-magnetic resonance imaging (DSA-MRI) system, etc. It should be noted that the medical system described below is merely provided for illustration purposes, and not intended to limit the scope of the present disclosure.

For illustration purposes, the present disclosure mainly describes systems and methods relating to an MRI system. It should be noted that the MRI system described below is merely provided as an example, and not intended to limit the scope of the present disclosure. The systems and methods disclosed herein may be applied to any other imaging systems.

It should be noted that user information (e.g., user device information, user personal information, etc.) and/or data (e.g., data used for analysis, data used for storing, data used for display, etc.) in the present disclosure are fully authorized by the user and/or multiple parties.

During a magnetic resonance (MR) scan, unwanted interference signals can be collected together with imaging signals (e.g., MR signals) by an MRI system, which reduces the image quality of MR image(s) generated based on the imaging signals. In order to improve the image quality of the MR images, the effect of the unwanted interference signals needs to be reduced and/or eliminated.

The present disclosure relates to systems and methods for signal processing. The methods may include obtaining initial signals and first interference signals collected in a time window of an MR scan of a target subject. The initial signals may be collected by a receiver coil of an MRI device when the target subject is in an excited state, and the first interference signals may be collected by an interference signal acquisition device. The methods may include determining target imaging signals included in the initial signals by processing the initial signals and the first interference signals using a prediction model. The methods may further include generating a target MR image of the target subject based on the target imaging signals. Therefore, the target imaging signals included in the initial signals can be determined automatically through the prediction model, which can improve the efficiency and accuracy of the target imaging signal determination, thereby improving the efficiency and accuracy of the target MR image.

In addition, the prediction model may include a first prediction model and/or a second prediction model. Different pre-trained prediction models may be provided for different types and/or degrees of interference signals, and the first prediction model can be determined from the pre-trained prediction models based on feature information of the first interference signals. Therefore, the degree of matching degree between the first prediction model and the first interference signals can be improved, which can further improve the accuracy of the target imaging signal determination. The second prediction model can be determined by training an initial prediction model based on an adversarial learning algorithm. Therefore, the relationship between the unwanted interference signals and the imaging signals in the initial signal can be considered, which can improve the accuracy of the target imaging signal prediction.

Moreover, a federated learning system is provided for training and maintaining the prediction model (e.g., the first prediction model and/or the second prediction model). For example, the federated learning system may include a central server and client devices communicatively connected with the central server. The central server may be configured to maintain a global prediction model for signal prediction, and each of the client devices may be configured to maintain a local prediction model for signal prediction corresponding to at least one MRI device. When one local prediction model is updated, each prediction model (including the local prediction models and the global prediction model) in the federated learning system can be updated, which can adequately mine the complex relationship among the initial signals, the first interference signals, the target imaging signals, and the unwanted interference signals, thereby improving the accuracy of the signal prediction. In addition, data (e.g., first model information and/or second model information) transmitted in the federated learning system do not require information relating to the target subject, which can protect the privacy of the target subject. As used herein, the first prediction model and/or the second prediction model can be regarded as the local prediction model or the global prediction model in the federated learning system. Correspondingly, the first prediction model and/or the second prediction model can be updated federally, which can improve the prediction accuracy of the first prediction model and/or the second prediction model.

FIG. 1 is a schematic diagram illustrating an exemplary signal processing system 100 according to some embodiments of the present disclosure. For illustration purposes, the signal processing system 100 illustrated in FIG. 1 may be an MRI system. As shown in FIG. 1, the MRI system may include an MRI device 110, a network 120, one or more terminals 130, a processing device 140, a storage device 150, and an interference signal acquisition device 160. In some embodiments, the MRI device 110, the terminal(s) 130, the processing device 140, the storage device 150, and/or the interference signal acquisition device 160 may be connected to and/or communicate with each other via a wireless connection (e.g., the network 120), a wired connection, or a combination thereof. The connection between the components in the signal processing system 100 may be variable.

The MRI device 110 may be configured to generate or provide imaging data (e.g., MR signals) by scanning a target subject or at least a part of the target subject. For example, the MRI device 110 may include a receiver coil, and the receiver coil of the MRI device 110 may collect initial signals in a time window of a magnetic resonance (MR) scan of the target subject when the target subject is in an excited state. In some embodiments, the receiver coil may include imaging coils, radio frequency (RF) coils, etc. The RF coils may include volume transmitting coils (VTCs), local acquisition coils (e.g., surface coils), or the like, or any combination thereof, for detecting the imaging data (e.g., the MR signals). The surface coils may be located closer to the region of the target subject being imaged than the VTCs. The VTCs and/or the surface coils may include a birdcage coil, a solenoid coil, a saddle coil, a Helmholtz coil, an array coil, a loop coil, a Rogowski (RO) coil, etc. The surface coils may include different specialized coils (e.g., head coil(s), spin coil(s), body surface coil(s), neck coil(s), limb coil(s), etc.) for different parts of the target subject. The surface coils may be detachably arranged on the MRI device 110 or the target subject.

In some embodiments, when signal interference (e.g., electromagnetic interference (EMI), radio frequency (RF) interference, etc.) exists during the MR scan, the receiver coil may also collect interference signals (also referred to as unwanted interference signals) in the MR scan. In other words, the initial signals collected by the receiver coil in the MR scan may include the MR signals (i.e., imaging signals) and the unwanted interference signals that need to be removed.

When no signal interference exists during the MR scan, the receiver coil may collect no unwanted interference signals in the MR scan. In other words, the initial signals collected by the receiver coil in the MR scan may only include the MR signals.

The interference signal acquisition device 160 may be configured to collect interference signals (also referred to as first interference signals) during the MR scan, wherein the first interference signals are used to estimate the unwanted interference signals for correcting the initial signals to determine the imaging signals collected during the MR scan. For example, when the signal interference exists during the MR scan, the interference signal acquisition device 160 may collect the first interference signals in the MR scan. As another example, when no signal interference exists during the MR scan, the interference signal acquisition device 160 may collect white noise in the MR scan. That is, no interference signals may be collected.

In some embodiments, the interference signal acquisition device 160 may include one or more interference signal acquisition coils. In some embodiments, the interference signal acquisition device 160 may be disposed in various manners. For example, the interference signal acquisition device 160 may be integrated with the MRI device 110. For instance, the one or more interference signal acquisition coils and the receiver coil may be integrated as a coil assembly. As another example, the interference signal acquisition device 160 may be disposed separately from the MRI device 110. For instance, the interference signal acquisition device 160 may be disposed outside of the MRI device 110, for example, on a wall of a room where the MRI device 160 is located.

In some embodiments, relationships between the above signals may be shown in Table 1.

TABLE 1

Relationships Between Signals

| Signal | When signal interference exists, and the target subject is in an excited state | When no signal interference exists, and the target subject is in the excited state | When signal interference exists, and the target subject is in an unexcited state |
|---|---|---|---|
| Se | First Interference Signals | White Noise | Third Interference Signals |
| Sc | Sci and Sce | Sci | Second Interference Signals |

In Table 1, "Se" may indicate signals collected by the interference signal acquisition device 160, "Sc" may indicate signals collected by the receiver coil of the MRI device 110, "Sci" may indicate the MR signals (i.e., the imaging signals) collected by the receiver coil of the MRI device 110, and "Sce" may indicate interference signals (i.e., the unwanted interference signals) collected by the receiver coil of the MRI device 110. For instance, when the signal interference exists during the MR scan, and the target subject is in the excited state, "Se" collected by the interference signal acquisition device 160 may be the first interference signals, and "Sc" collected by the receiver coil may include "Sci" and "Sce." That is, "Sc" may be the superposition of the imaging signals and the unwanted interference signals. When no signal interference exists during the MR scan, and the target subject is in the excited state, "Se" collected by the interference signal acquisition device 160 may be the white noise, and "Sc" collected by the receiver coil may be "Sci." That is, "Sc" may be the imaging signals. When the signal interference exists, and the target subject is in the unexcited state, "Se" collected by the interference signal acquisition device 160 may be third interference signals, and "Sc" collected by the receiver coil may be second interference signals.

The target subject may include patients or other experimental subjects (e.g., experimental mice or other animals). In some embodiments, the target subject may be a patient or a specific portion, organ, and/or tissue of the patient. For example, the target subject may include the head, the neck, the thorax, the heart, the stomach, a blood vessel, soft tissue, a tumor, nodules, or the like, or any combination thereof. In some embodiments, the target subject may be non-biological. For example, the target subject may include a phantom, a man-made object, etc.

The network 120 may include any suitable network that can facilitate the exchange of information and/or data for the signal processing system 100. In some embodiments, one or more components (e.g., the MRI device 110, the terminal 130, the processing device 140, the storage device 150, the interference signal acquisition device 160, etc.) of the signal processing system 100 may communicate information and/or data with one or more other components of the signal processing system 100 via the network 120. For example, the processing device 140 may obtain the imaging data from the MRI device 110 via the network 120. As another example, the processing device 140 may obtain user instructions from the terminal 130 via the network 120. In some embodiments, the network 120 may include one or more network access points.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the terminal(s) 130 may be part of the processing device 140.

The processing device 140 may process data and/or information obtained from one or more components (the MRI device 110, the terminal(s) 130, the storage device 150, and/or the interference signal acquisition device 160) of the signal processing system 100. For example, the processing device 140 may obtain the initial signals and the first interference signals collected in the time window of the MR scan of the target subject. As another example, the processing device 140 may obtain a prediction model (e.g., a global prediction model, a local prediction model, a first prediction model, a second prediction model, etc.). As still another example, the processing device 140 may determine the imaging signals included in the initial signals based on the prediction model and the first interference signals. As yet another example, the processing device 140 may generate a target MR image of the target subject based on the target imaging signals. In some embodiments, the processing device 140 may be a single server or a server group. The server group may be centralized or distributed. In some embodiments, the processing device 140 may be local or remote. In some embodiments, the processing device 140 may be implemented on a cloud platform.

In some embodiments, the processing device 140 may be implemented by a computing device. For example, the computing device may include a processor, a storage, an input/output (I/O), and a communication port. The processor may execute computer instructions (e.g., program codes) and perform functions of the processing device 140 in accordance with the techniques described herein. The computer instructions may include, for example, routines, programs, objects, components, data structures, procedures, modules, and functions, which perform particular functions described herein. In some embodiments, the processing device 140, or a portion of the processing device 140 may be implemented by a portion of the terminal 130.

The storage device 150 may store data/information obtained from the MRI device 110, the terminal(s) 130, and/or any other component of the signal processing system 100. In some embodiments, the storage device 150 may include a mass storage, a removable storage, a volatile read-and-write memory, a read-only memory (ROM), or the like, or any combination thereof. In some embodiments, the storage device 150 may store one or more programs and/or instructions to perform exemplary methods described in the present disclosure.

In some embodiments, the signal processing system 100 may include one or more additional components and/or one or more components of the signal processing system 100 described above may be omitted. Additionally or alternatively, two or more components of the signal processing system 100 may be integrated into a single component. A component of the signal processing system 100 may be implemented on two or more sub-components.

In some embodiments, the signal processing system 100 (e.g., the processing device 140) may serve as a central server configured to maintain the global prediction model for signal prediction. In some embodiments, the signal processing system 100 (e.g., the processing device 140) may serve as a client device configured to maintain the local prediction model for signal prediction. In some embodiments, the processing device 140 may serve as the central server, and the terminal(s) 130 may serve as client device(s). More descriptions regarding the maintenance of the global prediction model and/or the local prediction model may be found elsewhere in the present disclosure. See, e.g., FIGS. 9-12 and relevant descriptions thereof.

Figure 2:
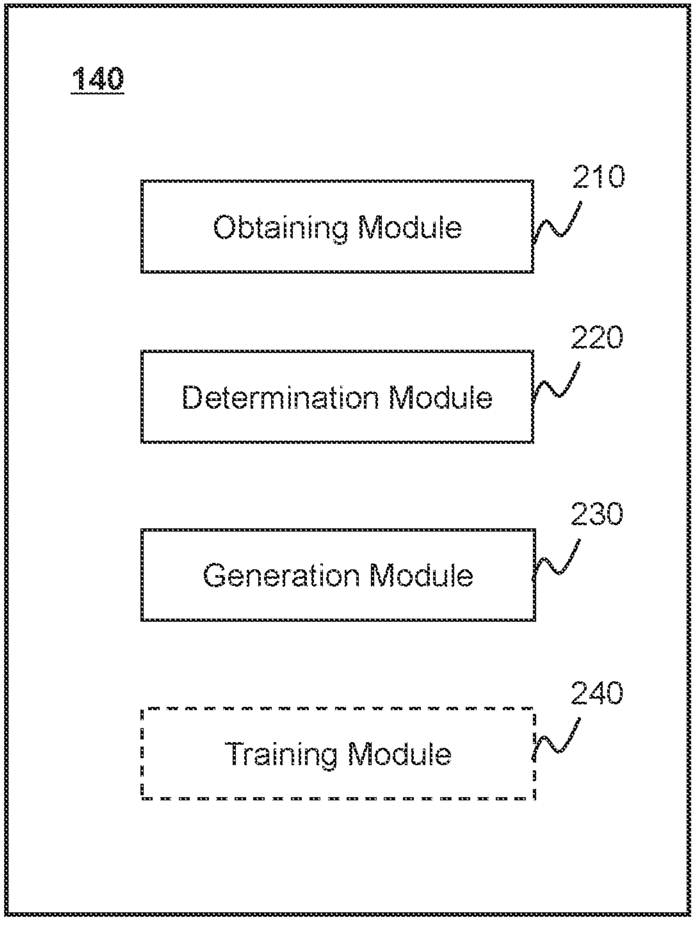
FIG. 2 is a block diagram illustrating an exemplary processing device according to some embodiments of the present disclosure.

FIG. 2 is a block diagram illustrating an exemplary processing device 140 according to some embodiments of the present disclosure. The modules illustrated in FIG. 2 may be implemented on the processing device 140. In some embodiments, the processing device 140 may be in communication with a computer-readable storage medium (e.g., the storage device 150 illustrated in FIG. 1) and execute instructions stored in the computer-readable storage medium. The processing device 140 may include an obtaining module 210, a determination module 220, and a generation module 230.

The obtaining module 210 may be configured to obtain initial signals and first interference signals collected in a time window of a magnetic resonance (MR) scan of a target subject when the target subject is in an excited state. In some embodiments, the initial signals may be collected by a receiver coil of an MRI device, and the first interference signals may be collected by an interference signal acquisition device in the time window of the MR scan. More descriptions regarding the obtaining of the initial signals and the first interference signals may be found elsewhere in the present disclosure. See, e.g., operation 302 and relevant descriptions thereof.

The determination module 220 may be configured to determine target imaging signals included in the initial signals by processing the initial signals and the first interference signals using a prediction model. The target imaging signals refer to imaging signals used for generating the image(s) of the target subject. In some embodiments, the prediction model may include a first prediction model for interference signal prediction, and the determination module 220 may determine the target imaging signals included in the initial signals based on the first prediction model and the first interference signals. In some embodiments, the prediction model may include a second prediction model, and the determination module 220 may determine the target imaging signals included in the initial signals by processing the initial signals and the first interference signals using the second prediction model. More descriptions regarding the determination of the target imaging signals included in the initial signals may be found elsewhere in the present disclosure. See, e.g., operation 304 and relevant descriptions thereof.

The generation module 230 may be configured to generate a target MR image of the target subject based on the target imaging signals. More descriptions regarding the generation of the target MR image may be found elsewhere in the present disclosure. See, e.g., operation 306 and relevant descriptions thereof.

In some embodiments, the processing device 140 may further include a training module 240. The training module 240 may be configured to generate one or more machine learning models used for signal prediction, such as, a global prediction model, a local prediction model, a first prediction model, a second prediction model, etc. In some embodiments, the training module 240 may be implemented on the processing device 140 or a processing device other than the processing device 140. In some embodiments, the training module 240 and other modules (e.g., the obtaining module 210, the determination module 220, the generation module 230, etc.) may be implemented on a same processing device (e.g., the processing device 140). Alternatively, the training module 240 and other modules (e.g., the obtaining module 210, the determination module 220, the generation module 230, etc.) may be implemented on different processing devices. For example, the training module 240 may be implemented on a processing device of a vendor of the machine learning model(s), while the other modules may be implemented on a processing device of a user of the machine learning model(s).

It should be noted that the above descriptions of the processing device 140 are provided for the purposes of illustration, and are not intended to limit the scope of the present disclosure. For persons having ordinary skills in the art, various variations and modifications may be conducted under the guidance of the present disclosure. However, those variations and modifications do not depart from the scope of the present disclosure. In some embodiments, the processing device 140 may include one or more other modules. For example, the processing device 140 may include a storage module to store data generated by the modules in the processing device 140. In some embodiments, any two of the modules may be combined as a single module, and any one of the modules may be divided into two or more units.

Figure 3:
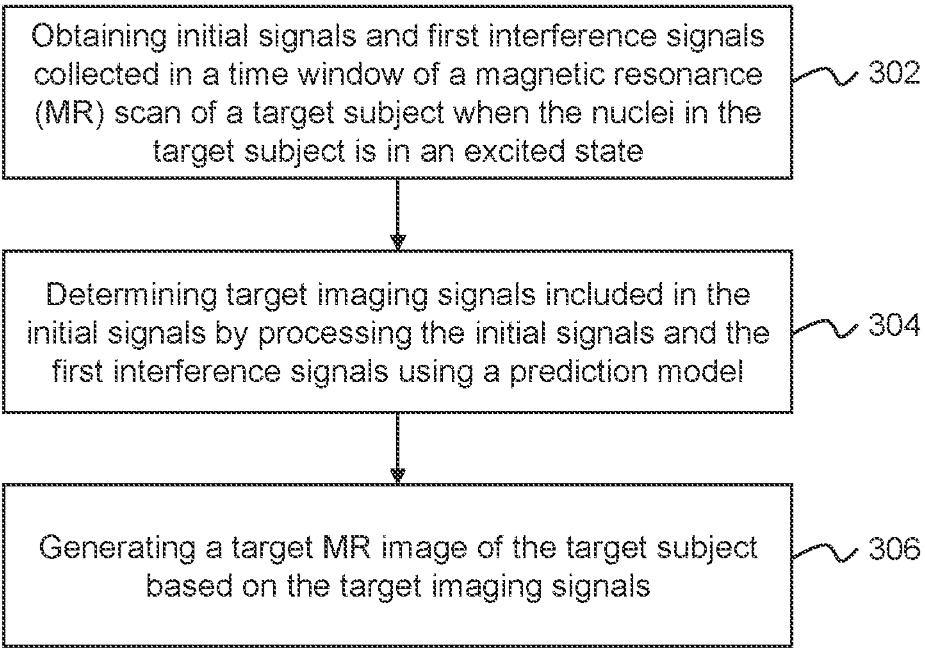
FIG. 3 is a flowchart illustrating an exemplary process for signal processing according to some embodiments of the present disclosure.

FIG. 3 is a flowchart illustrating an exemplary process 300 for signal processing according to some embodiments of the present disclosure. Process 300 may be implemented in the signal processing system 100 illustrated in FIG. 1. For example, the process 300 may be stored in the storage device 150 in the form of instructions (e.g., an application), and invoked and/or executed by the processing device 140.

During an MR scan, signal interference (e.g., EMI, RF interference, etc.) often affects imaging signals (e.g., MR signals) collected by an MRI device, which reduces the image quality of MR image(s) generated based on the imaging signals.

In some embodiments, the signal interference is reduced or eliminated by building a shielding room to prevent the collection of interference signals during the MR scan. However, the construction cost and site requirement(s) of the shielding room are high. At the same time, the shielding room also reduces the mobility of the MRI device, for example, limiting an application of a bedside MRI. In order to improve the flexibility of the interference signal reduction, the process 300 may be performed.

In 302, the processing device 140 (e.g., the obtaining module 210) may obtain initial signals and first interference signals (also referred to as interference signals) collected in a time window of a magnetic resonance (MR) scan of a target subject when the target subject is in an excited state.

In some embodiments, the initial signals may be collected by a receiver coil of an MRI device. For example, during the MR scan, the processing device 140 may control the MRI device 110 to apply a scan sequence to excite the target subject. After the target subject is excited, the receiver coil of the MRI device 110 may be controlled to collect the initial signals in the time window. As used herein, the time window may refer to a time period when the MRI device 110 emits RF signals and the target subject is excited. The receiver coil may include a VTC or a local acquisition coil of the MRI device 110. More descriptions regarding the receiver coil may be found elsewhere in the present disclosure (e.g., FIG. 1 and the relevant descriptions thereof).

In some embodiments, when no signal interference exists during the MR scan, the initial signals may include imaging signals received by the receiver coil in the time window. The imaging signals refer to signals collected by an imaging device (e.g., the MRI device 110) and used to generate image(s) of the target subject. For example, the imaging signals may be MR signals used to generate an MR image of the target subject. It should be noted that, the MR scan and/or the MR signals are merely provided for illustration, and not intended to limit the scope of the present disclosure. For example, the scan of the target subject may be a CT scan, and the imaging signals may be CT signals.

In some embodiments, when signal interference exists during the MR scan, the initial signals may include the imaging signals and unwanted interference signals received by the receiver coil in the time window. The signal interference may be caused by other electronic devices, natural environment, etc., for example, mobile phones, computers, metals, RF devices, etc.

The unwanted interference signals refer to signals that can affect the image quality of the image(s) generated based on the initial signals. For example, when the initial signals include the unwanted interference signals, the image(s) generated based on the initial signals may include artifacts, and/or the definition of the image(s) may be reduced, thereby reducing the image quality of the generated image(s). Exemplary interference signals may include electromagnetic interference (EMI) signals, audio interference signals, radio frequency (RF) interference signals, or the like, or any combination thereof.

In some embodiments, the first interference signals may be collected by an interference signal acquisition device in the time window of the MR scan. The interference signal acquisition device may include one or more interference signal acquisition coils. More descriptions regarding the interference signal acquisition device may be found elsewhere in the present disclosure (e.g., FIG. 1 and the relevant descriptions thereof). For example, during the MR scan, the interference signal acquisition device 160 may be controlled to receive the first interference signals (e.g., EMI signals, RF signals, etc.) in the time window.

In some embodiments, since the first interference signals are caused by the same reason as the unwanted interference signals, the first interference signals can be used to correct the initial signals (e.g., determine the unwanted interference signals included in the initial signals) in sequent operations. For example, a mapping relationship exists between the unwanted interference signals and the first interference signals, and the processing device 140 may predict the unwanted interference signals based on the mapping relationship and the first interference signals. Merely by way of example, a signal value of the first interference signals may be 50, and a signal value of the unwanted interference signals may be 25. That is, although the signal value of the first interference signals is different from the signal value of the unwanted interference signals, the signal value of the first interference signals and the signal value of the unwanted interference signals may correspond to a mapping relationship of 2:1, and the unwanted interference signals can be determined based on the mapping relationship and the first interference signals.

In some embodiments, the processing device 140 may obtain the initial signals from an imaging device (e.g., the MRI device 110) or a storage device (e.g., the storage device 150, a database, or an external storage) that stores the initial signals. For example, after the receiver coil of the MRI device 110 collects the initial signals, the initial signals may be stored in the storage device 150, and the processing device 140 may retrieve the initial signals from the storage device 150.

In some embodiments, the processing device 140 may obtain the first interference signals from an interference signal acquisition device (e.g., the interference signal device acquisition 160) or a storage device (e.g., the storage device 150, a database, or an external storage) that stores the first interference signals. For example, after the interference signal acquisition device 160 collects the first interference signals, the first interference signals may be stored in the storage device 150, and the processing device 140 may retrieve the first interference signals from the storage device 150.

In 304, the processing device 140 (e.g., the determination module 220) may determine target imaging signals included in the initial signals by processing the initial signals and the first interference signals using a prediction model.

The target imaging signals refer to imaging signals used for generating the image(s) of the target subject. In some embodiments, the target imaging signals may be obtained by removing the unwanted interference signals from the initial signals. For example, the initial signals may include MR signals (i.e., the imaging signals) and EMI signals (i.e., the unwanted interference signals), and signals (i.e., the MR signals) obtained by removing the EMI signals from the initial signals may be determined as the target imaging signals.

In some embodiments, the prediction model may include a first prediction model for interference signal prediction, and the processing device 140 may determine the target imaging signals included in the initial signals based on the first prediction model and the first interference signals. The first prediction model may be a trained machine learning model, which can determine unwanted interference signals included in the initial signals based on the first interference signals. The unwanted interference signals refer to interference signals in the initial signals that can reduce the image quality of the image(s) generated based on the initial signals and need to be removed from the initial signals.

In some embodiments, the processing device 140 may determine the first prediction model based on the first interference signals. For example, the processing device 140 may determine feature information of the first interference signals, and determine the first prediction model based on the feature information. More descriptions regarding the determination of the target imaging signals based on the first prediction model may be found elsewhere in the present disclosure (e.g., FIG. 4A and the descriptions thereof).

In some embodiments, the processing device 140 may determine the unwanted interference signals included in the initial signals based on the first prediction model and the first interference signals. For example, the processing device 140 may input the first interference signals (optionally with the initial signals) into the first prediction model, and the first prediction model may output the unwanted interference signals included in the initial signals. The processing device 140 may determine the target imaging signals based on the initial signals and the unwanted interference signals. For example, it is assumed that the initial signals are summation results of the target imaging signals and the unwanted interference signals, and the processing device 140 may determine the target imaging signals by subtracting the unwanted interference signals from the initial signals.

Merely by way of example, a receiver coil of an MRI device may collect 100 signal points in a time period, and each of the 100 signal points may include a first signal value of an imaging signal and a second signal value of an interference signal (i.e., an unwanted interference signal) corresponding to the signal point. If a signal value of one signal point in the 100 signal points is 500, and a second signal value of the signal point is 40, a first signal value of the signal point may be determined as 460 by subtracting the second signal value 40 from the signal value 500. Correspondingly, the target imaging signals may be determined by determining first signal values of the 100 signal points. As another example, the processing device 140 may determine the target imaging signals by processing the initial signals based on the unwanted interference signals and a signal correction algorithm.

In some embodiments, the prediction model may include a second prediction model, and the processing device 140 may determine the target imaging signals included in the initial signals by processing the initial signals and the first interference signals using the second prediction model. For example, the processing device 140 may input the initial signals and the first interference signals into the second prediction model, and the second prediction model may output the target imaging signals (and optionally with the unwanted interference signals). The second prediction model may also be referred to as a signal separation model that can separate the initial signals into the target imaging signals and the unwanted interference signals. When using the second prediction model, the assumption that the initial signals are the summation results of the target imaging signals and the unwanted interference signals is not applicable any more, and the complex relationship between the initial signals, the target imaging signals, and the unwanted interference signals are determined by the second prediction model. The unwanted interference signals may be used for model training (e.g., training the first prediction model), feature extraction, etc.

In some embodiments, the second prediction model may be a trained machine learning model, which can determine the target imaging signals included in the initial signals based on the initial signals and the first interference signals. Exemplary machine learning models may include a convolutional neural network (CNN) model, a recurrent neural network (RNN) model, a generative adversarial network (GAN) model, a u-net model, or the like, or any combination thereof.

In some embodiments, the processing device 140 may obtain the second prediction model from a storage device (e.g., the storage device 150) of the signal processing system 100 or a third-party database. In some embodiments, the second prediction model may be generated by the processing device 140 or another computing device according to a machine learning algorithm (e.g., adversarial learning algorithm). In some embodiments, the second prediction model may be generated by training an initial prediction model using training data. The training data may include sample data (as a training input) and reference data (as a training label), wherein the sample data includes sample initial signals and sample interference signals, and the reference data includes reference imaging signals and reference interference signals (and the sample interference signals). In some embodiments, the reference data may be regarded as ground truth data. More descriptions regarding the second prediction model may be found elsewhere in the present disclosure (e.g., FIGS. 5-7 and the descriptions thereof).

In some embodiments, the prediction model (e.g., the first prediction model, the second prediction model, etc.) may be a local prediction model corresponding to the MRI device or a global prediction model. Correspondingly, the processing device 140 may update the prediction model through a training system (e.g., the training system 900). More descriptions regarding the local prediction model and the global prediction model may be found elsewhere in the present disclosure (e.g., FIGS. 9-12 and the descriptions thereof).

In 306, the processing device 140 (e.g., the generation module 230) may generate a target MR image of the target subject based on the target imaging signals.

For example, the processing device 140 may generate the target MR image of the target subject by reconstructing the target imaging signals using an image reconstruction algorithm. Exemplary image reconstruction algorithms may include a Fourier reconstruction algorithm, a parallel reconstruction algorithm (e.g., a sensitivity encoding algorithm, a generalized auto-calibrating partially parallel acquisition (GRAPPA) algorithm, an iterative self-consistent parallel imaging reconstruction algorithm, a simultaneous multi-slice imaging algorithm, a 3D parallel reconstruction algorithm, etc.), a compressed sensing (CS) reconstruction algorithm, a deep learning-based reconstruction algorithm, or the like, or any combination thereof.

In some embodiments, the processing device 140 may display the target MR image of the target subject. For example, after the target MR image is generated, the processing device 140 may display the target MR image through a display screen (e.g., a display screen of the terminal(s) 130), and the user may obtain detection information from the target MR image. Exemplary display screens may include a liquid crystal display screen, an electronic ink display screen, etc.

According to some embodiments of the present disclosure, a prediction model is introduced for interference signal prediction. The prediction model is trained using a machine learning technique. In model training, the analysis of big data can enable mining the complex relationship among the initial signals, the first interference signals, the target imaging signals, and the unwanted interference signals, thus learning optimal mechanism(s) for determining the target imaging signals. Therefore, the target imaging signals included in the initial signals can be determined automatically, which can improve the efficiency and accuracy of the target imaging signal determination, thereby improving the efficiency and accuracy of the target MR image generation. In addition, by using the prediction model, the initial signals can be collected without the shielding room, which can reduce the construction cost and the usage threshold of the MRI device, thereby improving the flexibility and applicability of the MRI device.

Figure 4A:
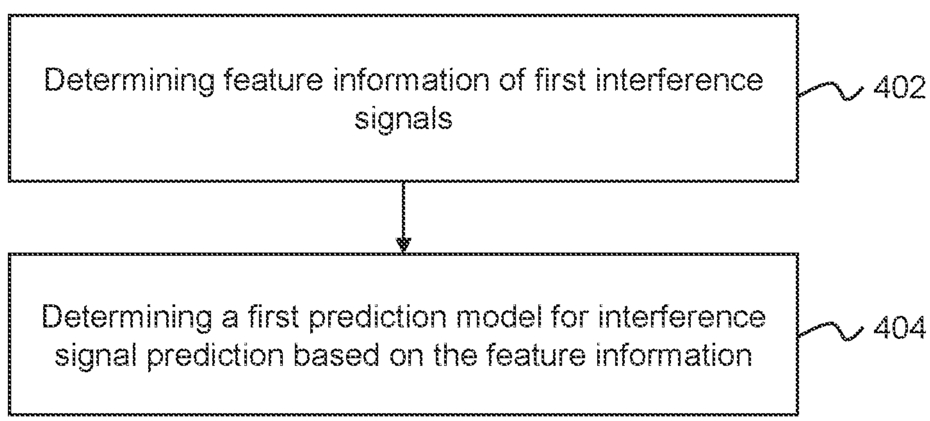
FIG. 4A is a flowchart illustrating an exemplary process for determining target imaging signals included in initial signals according to some embodiments of the present disclosure.

FIG. 4A is a flowchart illustrating an exemplary process 400A for determining target imaging signals included in initial signals according to some embodiments of the present disclosure. In some embodiments, the process 400A may be performed to achieve at least part of operation 304 as described in connection with FIG. 3.

In some embodiments, algorithms are introduced to reduce and/or correct interference signals collected during an MR scan. As an example, a machine learning model may be pre-trained for interference signal reduction. However, the pre-trained machine learning model is often suitable for common interference signals, but it is difficult for the pre-trained machine learning model to accurately predict severe/rare interference signals, which reduces the accuracy of the interference signal reduction. As another example, a machine learning model may be trained in real time to predict the interference signals collected during the MR scan. However, the real-time training requires additional acquisition time/computation resources, which reduces the efficiency of the interference signal reduction. In order to improve the efficiency and accuracy of the interference signal reduction, the process 400A may be performed.

In 402, the processing device 140 (e.g., the determination module 220) may determine feature information of first interference signals.

The feature information may indicate a category of the first interference signals. Exemplary feature information of the first interference signals may include an interference degree, an interference type, or the like, or any combination thereof, of the first interference signals.

The interference degree may indicate a degree of influence of the first interference signals on the image quality of image(s) generated based on initial signals. In some embodiments, the influences on the image quality may include influences on different dimensions of the image(s), such as, artifacts, definition, contrast, etc. Correspondingly, the interference degree may be represented in different manners based on the influences on different dimensions of the image(s). In some embodiments, the interference degree may be represented as words, numbers, letters, symbols, etc. For example, when the interference degree is represented as words, different interference degrees may correspond to different words, such as "slight interference," "moderate interference," "severe interference," "extremely severe interference," etc. As another example, when the interference degree is represented as numbers, different interference degrees may correspond to different numbers, such as 1, 2, 3, 5, 10, 20, etc. For instance, 1 may indicate slight interference, 2 may indicate moderate interference, 3 may indicate severe interference, 5, 10, 20, etc., may indicate different levels of extremely severe interference.

The interference type may refer to a signal type of the first interference signals. In some embodiments, the type of the first interference signals may be determined based on different classification manners. For example, the first interference signals may be classified into common interference signals, rare interference signals, infrequent interference signals, unknown interference signals, etc., according to a frequency of occurrence of the first interference signals. As another example, the first interference signals may be classified into EMI signals, audio interference signals, RF interference signals, etc., according to a source of the first interference signals. As still another example, the EMI signals may be divided into broadband interference source signals, narrowband interference source signals, etc., according to a band width of the first interference signals. As yet another example, the EMI signals may be divided into high-frequency EMI signals, low-frequency EMI signals, etc., according to a frequency of the first interference signals. As yet another example, the EMI signals may be divided into full frequency band interference signals, partial frequency band interference signals, certain frequency band interference signals, etc., according to a frequency band of the first interference signals.

In some embodiments, the processing device 140 may determine the feature information of the first interference signals by analyzing or processing the first interference signals. For example, the processing device 140 may classify and count amplitudes of the first interference signals to determine information (e.g., a signal strength, a dispersion degree, the amplitudes, etc.) of the first interference signals, so as to determine the feature information of the first interference signals.

As another example, the processing device may determine the feature information of the first interference signals using a feature discrimination model. The feature discrimination model may be a trained machine learning model, which can determine the feature information of the first interference signals based on the first interference signals. For example, the processing device 140 may input the first interference signals into the feature discrimination model, and the feature discrimination model may output the feature information of the first interference signals. The feature information of the first interference signals may include the interference degree and/or the interference type of the first interference signals. That is, the feature discrimination model may be used to simultaneously determine the interference degree and the interference type of the first interference signals. For example, the feature discrimination model may output that the feature information of the first interference signals is slight interference and common interference signals, the feature information of the first interference signals is severe interference and extremely severe interference signals, the feature information of the first interference signals is moderate interference and EMI signals, the feature information of the first interference signals is severe interference and RF interference signals, etc. Alternatively, the feature discrimination model may be used to separately determine the interference degree and the interference type of the first interference signals.

In some embodiments, when the interference type does not affect the MR scan, or the interference degree does not reduce the image quality of the generated image(s) (e.g., when the interference degree is relatively low, it can be considered that there are no interference signals), the feature discrimination model may output that the first interference signals are noise-free signals, or the processing device 140 may determine that the first interference signals are noise-free signals based on the interference type and/or the interference degree of the first interference signals output by the feature discrimination model.

In some embodiments, the feature discrimination model may be a single model. Exemplary feature discrimination models may include a neural network model, a support vector machine, a logistic regression model, a Bayesian model, or the like, or any combination thereof.

In some embodiments, the feature discrimination model may be generated by training a first initial model using a plurality of first training samples based on a model training algorithm (e.g., a gradient descent algorithm, etc.). Each of the plurality of first training samples may include sample interference signals of a sample subject (as a training input) and sample feature information (e.g., a sample interference degree and a sample interference type) of the sample interference signals (as a training label). The sample interference signals of the sample subject may be acquired in historical MR scan(s) of the sample subject. The sample feature information may be represented as a two-tuple, such as (S*, C*). As used herein, "S*" represents the sample interference degree, "C*" represents the sample interference type. When no interference signals exist, the corresponding label may be represented as (S0, C0). In some embodiments, the training label may be determined or confirmed by a user or other manners, which will not be limited herein.

By determining the feature information (e.g., the interference degree and the interference type) of the first interference signals using the single model, the process of the feature information determination can be simplified, and a count of models to be trained can be reduced, which can reduce consumption time, and improve the efficiency of the feature information determination, thereby improving the efficiency of the MR image generation. In addition, the single model is easy to maintain.

In some embodiments, the feature discrimination model may include a first feature discrimination model and a second feature discrimination model. The first feature discrimination model may be configured to determine the interference degree of the first interference signals, and the second feature discrimination model may be configured to determine the interference type of the first interference signals. In some embodiments, the first feature discrimination model and the second feature discrimination model may be two independent models. Alternatively, the first feature discrimination model and the second feature discrimination model may be combined to be a fusion model.

When the first feature discrimination model and the second feature discrimination model are used as two independent models, the processing device 140 may determine the interference degree by inputting the first interference signals into the first feature discrimination model and/or determine the interference type by inputting the first interference signals into the second feature discrimination model. Therefore, the first feature discrimination model and/or the second feature discrimination model can be flexibly selected according to an actual need.

In some embodiments, the first feature discrimination model and the second feature discrimination model may be trained in a similar manner to how to train the feature discrimination model. For example, the first feature discrimination model may be generated by training a second initial model using a plurality of second training samples based on a model training algorithm (e.g., a gradient descent algorithm, etc.). Each of the second training samples may include sample interference signals of a sample subject (as a training input) and a sample interference degree of the sample interference signals (as a training label). Similarly, the second feature discrimination model may be generated by training a third initial model using a plurality of third training samples based on a model training algorithm (e.g., a gradient descent algorithm, etc.). Each of the third training samples may include sample interference signals of a sample subject (as a training input) and a sample interference type of the sample interference signals (as a training label). In some embodiments, the second initial model and/or the third initial model may be the same as or different from the first initial model. In some embodiments, the second training samples and/or the third training samples may be the same as or different from the first training samples. For example, the second training samples and/or the third training samples may be a portion of the first training samples.

When the first feature discrimination model and the second feature discrimination model are used as a fusion model, the processing device 140 may input the first interference signals into the fusion model. The fusion model may determine the interference degree and the interference type of the first interference signals in sequence. For example, the first feature discrimination model of the fusion model may determine the interference degree of the first interference signals. The fusion model may determine whether interference signals exist according to the interference degree of the first interference signals. When the interference signals exist, the second feature discrimination model of the fusion model may output the interference type of the first interference signals. When no interference signals exist, the fusion model may output that the first interference signals are noise-free signals. In some embodiments, the fusion model may be trained in a similar manner to how to train the feature discrimination model, which will not be repeated herein.

By determining the feature information (e.g., the interference degree and the interference type) of the first interference signals through the first feature discrimination model and the second feature discrimination model, the process of the feature information determination is more flexible. For example, the two feature discrimination models can be used separately or combined according to certain rules. For instance, the first feature discrimination model may be used firstly. If an output of the first feature discrimination model indicates that no interference signals exist, the processing device 140 may directly perform operation 404 without using the second feature discrimination model, which can avoid unnecessary determination and improve the efficiency of the feature information determination. At the same time, each of the two feature discrimination models may only implement a single task, and the task corresponding to each of the two feature discrimination models may be simplified, which can improve the reliability of each of the two feature discrimination models. In addition, the first feature discrimination model and the second feature discrimination model may be run separately, which can reduce the memory consumption and errors when applying the two feature discrimination models, thereby improving the safety and robustness of the two feature discrimination models. Moreover, any one of the two feature discrimination models can be maintained and replaced without affecting the other model, which is convenient for modular upgrade and fault location.

In 404, the processing device 140 (e.g., the determination module 220) may determine a first prediction model for interference signal prediction based on the feature information.

The first prediction model may be a trained machine learning model, which can determine unwanted interference signals included in initial signals based on the first interference signals. Exemplary machine learning models may include a neural network model, a deep neural network model, a support vector machine, a convolutional neural network (CNN) model, a recurrent neural network (RNN) model, a generative adversarial network (GAN) model, a long short-term memory (LSTM) network model, an automatic encoder network model, a deep belief network (DBN) model, a deep residual network model, a gate recurrent unit (RGU) network model, an echo state network model, or the like, or any combination thereof. For example, the processing device 140 may input the first interference signals into the first prediction model, and the first prediction model may output the unwanted interference signals included in the initial signals.

In some embodiments, the first prediction model may be generated by the processing device 140 or another computing device by training an initial prediction model (e.g., a first initial prediction model) using a plurality of fourth training samples. Each of the plurality of fourth training samples may include sample interference signals of a sample subject (as a training input) and sample unwanted interference signals corresponding to the sample interference signals (as a training label).

In some embodiments, for a fourth training sample, the processing device 140 may obtain the sample interference signals of the sample subject of the training sample from an imaging device (e.g., the MRI device 110) or a storage device (e.g., the storage device 150, a database, or an external storage). For example, the sample interference signals may be obtained in a similar manner as how the first interference signals are obtained as described in operation 302. That is, when signal interference exists during an MR scan and the sample subject is in an excited state, first interference signals collected by the interference signal acquisition device 160 may be determined as the sample interference signals. As another example, when signal interference exists and the sample subject is in an unexcited state, third interference signals collected by the interference signal acquisition device 160 may be determined as the sample interference signals. Further, the processing device 140 may obtain the sample unwanted interference signals corresponding to the sample interference signals. For example, when the same signal interference exists during the MR scan and the sample subject is in the excited state, unwanted interference signals collected by the receiver coil of the MRI device 110 may be determined as the sample unwanted interference signals corresponding to the sample interference signals. As another example, when signal interference exists and the sample subject is in the unexcited state, second interference signals collected by the receiver coil of the MRI device 110 may be determined as the sample unwanted interference signals corresponding to the sample interference signals. As still another example, the processing device 140 may determine the sample unwanted interference signals based on a second prediction model and the sample interference signals. For instance, the processing device 140 may input the sample interference signals and corresponding sample initial signals into the second prediction model, and the second prediction model may output the sample unwanted interference signals. More descriptions regarding the second prediction model may be found elsewhere in the present disclosure (e.g., FIGS. 5-7 and the descriptions thereof).

In some embodiments, the processing device 140 may generate the first prediction model by training the first initial prediction model using the plurality of fourth training samples. For example, the training of the first initial prediction model may include an iterative process. The plurality of fourth training samples may be used to iteratively update model parameter(s) of the first initial prediction model until a termination condition is satisfied. Exemplary termination conditions may include that a value of a loss function corresponding to the first initial prediction model is below a threshold value, a difference of values of the loss function obtained in a previous iteration and the current iteration is within a threshold value, a certain count of iterations has been performed, etc. For example, in a current iteration, sample interference signals of a sample subject may be input into the first initial prediction model, and the first initial prediction model may output a prediction result (e.g., predicated interference signals). Then, a value of the loss function may be determined to measure a difference between the prediction result and the training label (e.g., sample unwanted interference signals corresponding to the sample interference signals). If it is determined that the termination condition is satisfied in the current iteration, the first initial prediction model may be designated as the first predicted model; otherwise, the first initial prediction model may be further updated based on the value of the loss function.

In some embodiments, the input of the first prediction model may further include the initial signals. That is, the first prediction model may determine the unwanted interference signals (e.g., the unwanted interference signals) included in initial signals based on the first interference signals and the initial signals. Correspondingly, each of the plurality of fourth training samples may further include sample initial signals of the sample subject. By using the sample initial signals of the sample subject to train the first initial prediction model, the first prediction model can learn the mapping relationship between the first interference signals and the initial signals can be improved, which improves the prediction performance (e.g., the prediction accuracy) of the first prediction model.

In some embodiments, the processing device 140 may determine the first prediction model from a plurality of pre-trained prediction models based on the feature information of the first interference signals. Merely by way of example, the processing device 140 may obtain a plurality of pre-trained prediction models and a corresponding relationship between the plurality of pre-trained prediction models and reference feature information, and determine the first prediction model from the plurality of pre-trained prediction models based on the feature information of the first interference signals and the corresponding relationship.

The corresponding relationship may be represented as a table, a diagram, a model, etc., or any form that can indicate the relationship between the plurality of pre-trained prediction models and the reference feature information. In some embodiments, the corresponding relationship between the plurality of pre-trained prediction models and the reference feature information may be pre-determined, and stored in a storage device (e.g., the storage device 150). The processing device 140 may obtain the corresponding relationship from the storage device. For example, the plurality of pre-trained prediction models may be generated by training the first initial prediction model using training samples corresponding to different reference feature information. Correspondingly, the corresponding relationship may be determined based on different reference feature information corresponding to the training samples. For instance, a first model is obtained using sample interference signals of "slight interference" and corresponding sample unwanted interference signals, a second model is obtained using sample interference signals of "moderate interference" and corresponding sample unwanted interference signals, a third model is obtained using sample interference signals of "severe interference" and corresponding sample unwanted interference signals, and a fourth model is obtained using sample interference signals of "extremely severe interference" and corresponding sample unwanted interference signals. The processing device 140 may determine that interference signals with an interference degree of "slight interference" correspond to the first model, interference signals with an interference degree of "moderate interference" correspond to the second model, interference signals with an interference degree of "severe interference" correspond to the third model, and interference signals with an interference degree of "extremely severe interference" correspond to the fourth model.

As another example, a first model is obtained using sample interference signals of "common interference signals" and corresponding sample unwanted interference signals, a second model is obtained using sample interference signals of "rare interference signals" and corresponding sample unwanted interference signals, and a third model is obtained using sample interference signals of "infrequent interference signals" and corresponding sample unwanted interference signals. The processing device 140 may determine that interference signals with an interference type of "common interference signals" correspond to the first model, interference signals with an interference type of "rare interference signals" correspond to the second model, interference signals with an interference type of "infrequent interference signals" correspond to the third model, and interference signals with an interference type of "unknown interference signals" correspond to no pre-trained models.

In some embodiments, interference signals with an interference degree of "extremely severe interference" and/or an interference type of "unknown interference signals" correspond to no pre-trained models. In some embodiments, one of the pre-trained models may need to be updated to process interference signals with an interference degree of "extremely severe interference" and/or an interference type of "unknown interference signals." In some embodiments, the corresponding relationship may be determined by the user according to actual requirement(s), which is not limited herein.

The processing device 140 may determine the first prediction model from the plurality of pre-trained prediction models based on the feature information and the corresponding relationship. For example, if the interference degree of the first interference signal is "slight interference," the processing device 140 may determine a pre-trained prediction model corresponding to "slight interference" as the first prediction model. As another example, if the interference type of the first interference signal is "rare interference signals," the processing device 140 may determine a pre-trained prediction model corresponding to "rare interference signals" as the first prediction model. As still another example, if the interference degree of the first interference signal is "extremely severe interference" and/or an interference type of the first interference signal is "unknown interference signals," the processing device 140 may determine that the pre-trained prediction model needs to be updated.

According to some embodiments of the present disclosure, the first prediction model may be determined from the plurality of pre-trained prediction models based on the feature information of the first interference signals. In this way, a model more suitable used for the current environment can be used for interference signal prediction, thereby improving the accuracy of the interference signal reduction.

In some embodiments, the processing device 140 may perform the process 400B to achieve operation 404.

In 410, the processing device 140 may determine whether the first interference signals are abnormal based on the feature information. Merely by way of example, when an interference degree of the first interference signals exceeds a preset threshold (also referred to as a first preset threshold) and/or an inference type of the first interference signals is an unknown interference type, the first interference signals may be determined to be abnormal. The preset threshold may be determined based on experience of the user or set manually by the user. For example, when the interference degree is represented as words, such as "slight interference," "moderate interference," "severe interference," "extremely severe interference," the interference degree of "severe interference" may be determined as the preset threshold. As another example, when the interference degree is represented as numbers, such as 1-20, the interference degree of 8 or 9 may be determined as the preset threshold. A relatively large value may indicate a relatively high interference degree.

In some embodiments, the processing device 140 may compare the interference degree of the first interference signals with the preset threshold, and then determine whether the first interference signals are abnormal based on the comparison result. For example, if the interference degree of the first interference signals is 5 and the preset threshold is 9, the processing device 140 may determine a comparison result that the interference degree does not exceed the preset threshold, and determine that the first interference signals are not abnormal. As another example, if the interference degree of the first interference signals is 10 and the preset threshold is 9, the processing device 140 may determine a comparison result that the interference degree exceeds the preset threshold, and determine that the first interference signals are abnormal.

If the first interference signals are not abnormal, the processing device 140 may perform operation 420 to determine a pre-trained prediction model as the first prediction model. For example, the processing device 140 may determine the first prediction model from the plurality of pre-trained prediction models based on the feature information and the corresponding relationship.

If the first interference signals are abnormal, the processing device 140 may perform operation 430 to determine the first prediction model by updating the pre-trained prediction model (e.g., any one of the pre-trained prediction models). In some embodiments, the processing device 140 may obtain new sample data, and update the pre-trained prediction model based on the new sample data. The new sample data refers to sample data that has not been used to train the pre-trained prediction model. In some embodiments, the new sample data may include signals collected in real time, signals collected in history and stored in the corresponding MRI device (e.g., the MRI device 110) or a storage device (e.g., the storage device 150), etc. For example, the processing device 140 may obtain second interference signals and third interference signals collected in a second time window of the MR scan of the target subject when the target subject is in the unexcited state. The subject may be in an unexcited state in the second time window. As used herein, a second time window may refer to a time period when the MRI device 110 is not emitting RF signals and the target subject is not excited. The second interference signals may be collected by the receiver coil of the MRI device, and the third interference signals may be collected by the interference signal acquisition device. The processing device 140 may update the pre-trained prediction mode based on the second interference signals and the third interference signals. For instance, the third interference signals may be determined as a training input, and the second interference signals may be determined as a training label. The pre-trained prediction model may be updated based on the new sample data in a similar manner to how the first prediction model is generated. In some embodiments, the processing device 140 may directly train an initial model using the second and third interference signals, and designated the trained model as the updated pre-trained prediction model.

In some embodiments, after determining that the first interference signals are abnormal, the processing device 140 may further perform operation 440 to determine whether the interference degree of the first interference signals exceeds a second preset threshold. The second preset threshold may be higher than the first preset threshold. For example, the first preset threshold may be severe interference, and the second preset threshold may be extremely severe interference. As another example, the first preset threshold may be moderate interference, and the second preset threshold may be severe interference or extremely severe interference. As still another example, the first preset threshold may be 9, and the second preset threshold may be 15. In some embodiments, the second preset threshold may be determined based on experience of the user or set manually by the user. For example, the second preset threshold may be determined based on historical processing results of historical initial signals. For instance, if the historical processing results indicate that when the interference degree of the first interference signals exceeds a certain threshold, it is different to reduce unwanted interference signals in the historical initial signals, the certain threshold may be determined as the second preset threshold.

If the interference degree of the first interference signals exceeds the second preset threshold, the processing device 140 may perform operation 450 to determine that the initial signals need to be re-collected or the initial signals need to be removed.

The re-collection the initial signals may be performed by performing a new scan on the target subject to obtain new signals. For example, the processing device 140 may direct the receiver coil of the MRI device to perform a new scan on the target subject to obtain new signals.

When the initial signals are removed, interference reduction may not need to be performed on the initial signals and the initial signals may not be used in subsequent image reconstruction. In some embodiments, corrected initial signals may be determined (e.g., interpolated and/or estimated) based on other initial signals according to reconstruction algorithm(s). By using the reconstruction algorithm(s) to estimate the corrected initial signals, the influence of the first interference signals on the image quality of the generated image(s) can be reduced.

In some embodiments, some interference signals may have a great influence on the image quality of the generated image(s) due to various reasons, but it is difficult to remove these interference signals from the initial signals. For example, if the initial signals pass through the center of K space, and the unwanted interference signals cannot be removed, the image quality of the generated image(s) may be reduced greatly. At this time, the initial signals may need to be re-collected or removed, which can avoid the image quality of the generated image(s) from being reduced.

In some embodiments, when the first prediction model is determined or new sample data is obtained, the processing device 140 may determine whether the first prediction model needs to be updated. More descriptions regarding the determination of whether the first prediction model needs to be updated may be found elsewhere in the present disclosure (e.g., FIG. 8 and the descriptions thereof).

According to some embodiments of the present disclosure, different pre-trained prediction models may be provided for different types and/or degrees of interference signals, and the first prediction model can be determined from the plurality of pre-trained prediction models based on the feature information of the first interference signals.

Therefore, the matching degree between the first prediction model and the first interference signals can be improved, which can reduce additional acquisition time/computation for real-time model training, thereby improving the accuracy of the interference signal reduction. In addition, a plurality of signal processing strategies (e.g., determining the first prediction model from the plurality of pre-trained prediction models, updating the pre-trained prediction model, re-collecting the initial signals, setting the initial signals as non-acquisition, etc.) can be selected according to the feature information of the first interference signals, which can improve the flexibility, efficiency, and accuracy of the target imaging signal determination.

Figure 5:
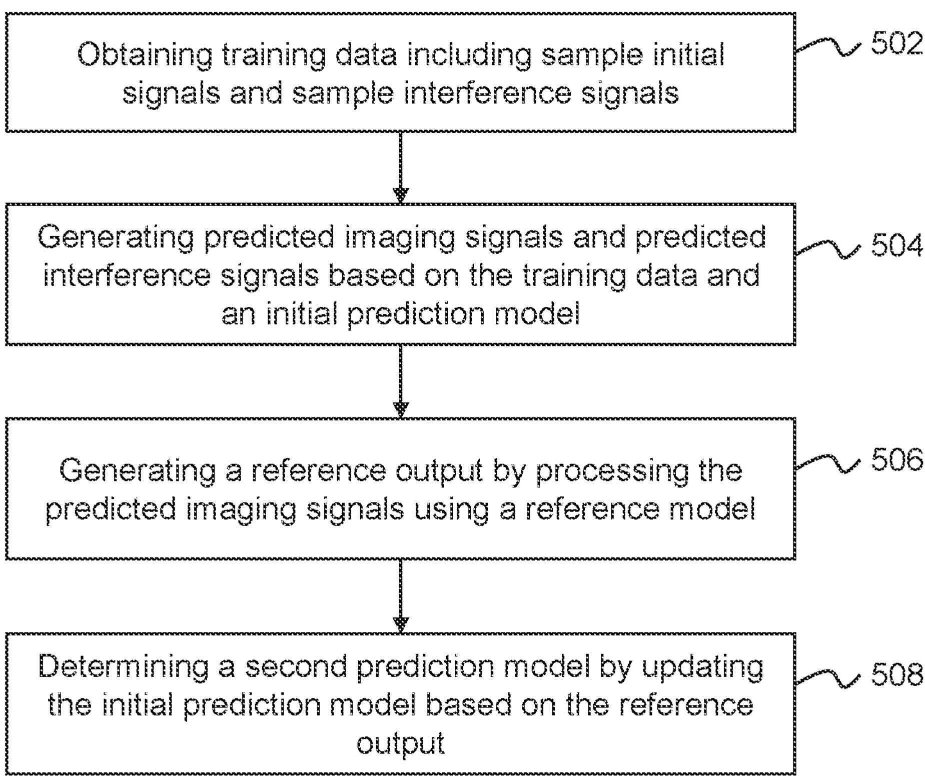
FIG. 5 is a flowchart illustrating an exemplary process for determining a second prediction model according to some embodiments of the present disclosure.

FIG. 5 is a flowchart illustrating an exemplary process 500 for determining a second prediction model according to some embodiments of the present disclosure. In some embodiments, the process 500 may be performed to achieve at least part of operation 304 as described in connection with FIG. 3.

In some embodiments, interference signal reduction is performed by estimating the unwanted interference signals in the initial signals, and determining the target imaging signals by subtracting the unwanted interference signals from the initial signals. However, in some occasions, a relationship between the unwanted interference signals and the target imaging signals is complex and the initial signals may not be equal to the sum of the target imaging signals and the unwanted interference signals. For example, it is assumed that a maximum signal value detected by the receiver coil is 1100. When a signal value of an unwanted interference signal is 500, and a signal value of a target imaging signal is 600, a signal value detected by the receiver coil is 1100. When a signal value of an unwanted interference signal is 500, and a signal value of a target imaging signal is 800, a signal value detected by the receiver coil is still 1100. In such cases, the target imaging signals determined by subtracting the unwanted interference signals from the initial signals have a relatively low accuracy. In addition, it is hard for the receiver coil to collect pure imaging signals without interference signals or collect the unwanted interference signals without the imaging signals when the sample subject is excited, which causes that a prediction model for interference signal prediction can only be trained based on the interference signals collected in the non-imaging period, which limits the sample data that can be used in the model training.

In order to solve the above problems, the process 500 may be performed to provide a second prediction model for signal prediction. The second prediction model may be a signal separation model that can directly determine the target imaging signals in the initial signals, for example, it can separate the initial signals into the target imaging signals and the unwanted interference signals.

In 502, the processing device 140 (e.g., the training module 240) may obtain training data including sample initial signals and sample interference signals.

The training data refers to data used to train a second prediction model.

In some embodiments, the sample initial signals and the sample interference signals may be obtained in a similar manner as how the initial signals and the first interference signals are obtained as described in operation 302. For example, the sample initial signals and the sample interference signals may be a portion of historical data. As another example, the sample initial signals and the sample interference signals may be collected by a receiver coil of an MRI device (e.g., the MRI device 110) and an interference signal acquisition device (e.g., the interference signal acquisition device 160), respectively, in a sample MR scan of a sample subject when the sample subject is excited.

In some embodiments, the training data may be the same as the plurality of training samples used to train the first prediction model.

In some embodiments, the sample initial signals and the sample interference signals may have a corresponding relationship. The corresponding relationship refers to that a type of the sample interference signals is the same as a type of interference signals in the sample initial signals. For example, the sample interference signals and the interference signals in the sample initial signals are EMI signals. In some embodiments, the corresponding relationship refers to that a place where the sample interference signals are collected is the same as a place where the sample initial signals are collected.

In some embodiments, the processing device 140 may obtain the sample initial signals from an imaging device (e.g., the MRI device 110) or a storage device (e.g., the storage device 150, a database, or an external storage) that stores the sample initial signals. In some embodiments, the processing device 140 may obtain the sample interference signals from an interference signal acquisition device (e.g., the interference signal acquisition device 160) or a storage device (e.g., the storage device 150, a database, or an external storage) that stores the sample interference signals.

In 504, the processing device 140 (e.g., the training module 240) may generate predicted imaging signals and predicted interference signals based on the training data and an initial prediction model.

In some embodiments, the initial prediction model (also referred to as a second initial prediction model) may be an initial model (e.g., a model whose parameters are obtained by randomization), or a pre-trained model (e.g., a model that has been trained based on a public data set or a portion of the training data).

The predicted imaging signals may refer to imaging signals separated from the sample initial signals by the second initial prediction model. The predicted interference signals may refer to interference signals separated from the sample initial signals by the second initial prediction model.

In some embodiments, the processing device 140 may input the training data (e.g., the sample initial signals and the sample interference signals) into the initial prediction model, and the initial prediction model may output the predicted imaging signals and the predicted interference signals. For example, assuming that a signal value of the sample initial signals is 1000, and a signal value of the sample interference signals is 200, after the sample initial signals and the sample interference signals are input into the initial prediction model, the initial prediction model may output that a signal value of the predicted imaging signals is 800, and a signal value of the predicted interference signals is 200. It should be noted that, since a relationship between the unwanted interference signals and the target imaging signals in the initial signals is complex, the sum of the signal values of the predicted interference signals and the predicted imaging signals output by the initial prediction model may not be necessarily equal to the signal value of the sample initial signals. For example, the initial prediction model may output that the signal value of the predicted imaging signals is 750, and the signal value of the predicted interference signals is 150. That is, the sum of the signal values of the predicted interference signals and the predicted imaging signals is 900, which is different from 1000.

In 506, the processing device 140 (e.g., the training module 240) may generate a reference output by processing the predicted imaging signals using a reference model.

In some embodiments, the processing device 140 may train the initial prediction model based on an adversarial learning algorithm. The adversarial learning algorithm may use two networks to compete with each other, one of which is a generation network and the other is a discrimination network. The generation network generates predicted data. The predicted data is input into the discrimination network, and the discrimination network discriminates whether the predicted data is real or fake. In some embodiments, a training goal of the adversarial learning algorithm is to make the generation network to output predicted data that can fool the discrimination network, and/or make the discrimination network to have a good discrimination capability.

In some embodiments, the generation network in the adversarial learning algorithm may be the second prediction model, and the discrimination network may be used as the reference model. The discrimination network may be configured to generate the reference output by determining whether the predicted imaging signals and/or the predicted interference signals are real or not.

In some embodiments, the discrimination model (i.e., the reference model) may include a classification model, for example, a fully connected network, etc., which can be used to determine the probability that sample data input into the discrimination model is from the real training data (i.e., determining the probability that the input sample data is not generated by the generation network). If the input sample data is the real sample training data, the discrimination model may output a large probability. Otherwise, the discrimination model may output a small probability.

In some embodiments, the discrimination model may be used to determine the probability that the predicted imaging signals and/or the predicted interference signals are from a real training data set, and the real training data set may include a pure imaging signal data set and a pure interference signal data set. Sample data in the pure imaging data set may be referred to as pure imaging signals, and the pure imaging signals may be MR signals collected by a receiver coil of an MRI device (e.g., the MRI device 160) when no signal interference exists in the environment (i.e., under an interference-free environment). Sample data in the pure interference signal data set may be referred to as pure interference signals. The pure interference signals may be interference signals collected by a sample receiver coil of a sample MRI device when the signal interference exists in the environment and the sample subject is in an unexcited state (or interference signals collected during a non-MRI time period).

In some embodiments, the sample data in the pure imaging signal data set may be collected from different subjects and different environments, and the sample data in the pure interference signal data set may be collected in the same environment from the same subject as the sample data in the pure imaging signal data set. That is, the sample data in the pure interference signal data set can be collected when corresponding sample data in the pure imaging signals is collected.

In some embodiments, the discrimination model (i.e., the reference model) may be a binary classification model or a multi-classification model. When the discrimination model is a binary classification model, the discrimination model may discriminate whether the predicted imaging signals or the predicted interference signal is real or generated by the second prediction model. When the discrimination model is a multi-classification model, the discrimination model may discriminate the types of the input signals, such as the pure interference signals, the predicted interference signals, the pure imaging signals, and the predicted imaging signals. For example, when the discrimination model is a four-classification model, the discrimination model may be used to determine a type of the input signals as one of the real interference signals, the predicted/synthesized interference signals, the real imaging signals, or the predicted/synthesized imaging signals. In some embodiments, when the discrimination model is a binary classification model, the discrimination model may also simultaneously discriminate the types and authenticity of various input signals, such as the pure interference signals, the predicted interference signals, the pure imaging signals, and the predicted imaging signals.

In some embodiments, the discrimination model may include one or more discrimination networks.

In some embodiments, the discrimination model (i.e., the reference model) may include a first discrimination model (e.g., a first discrimination model), and the training data may further include pure imaging signals collected under an interference-free environment. For example, the sample initial signals may be collected by the receiver coil when the sample subject is excited in an environment with sample interference signals, and the pure imaging signals may be collected the same environment after the interference signals are removed (e.g., by removing the source of the sample interference signals, or utilization an interference signal shielding device). The processing device 140 may input the predicted imaging signals and/or the pure imaging signals into the first discrimination model to determine the reference output. The reference output may include a first discrimination result relating to the sample imaging signals and the predicted imaging signals. For example, the first discrimination result output by the first discrimination model may include a determination result of whether the predicted imaging signals are the real imaging signal, a probability that the predicted imaging signals are from the pure imaging signal data set, etc.

In some embodiments, the discrimination model (i.e., the reference model) may include a second discrimination model (e.g., a second discrimination model). The training data may further include pure interference signals collected by a sample receiver coil when the sample subject is in an unexcited state. For example, the pure interference signals may be collected in the same environment as the sample initial signals except that the sample subject is excited in the collection of the sample initial signals and the sample subject is not excited in the collection of the pure interference signals. The processing device 140 may input the predicted interference signals and/or the pure interference signals into the second discrimination model to determine the reference output. The reference output may include a second discrimination result relating to the pure interference signals and the predicted interference signals. For example, the second discrimination result output by the second discrimination model may include a determination result of whether the predicted interference signals are the real interference signal, a probability that the predicted interference signals are from the pure interference signal data set, etc.

In some embodiments, the first discrimination model and the second discrimination model may be binary classification models. Further, the second prediction model may be trained based on the first discrimination result and the second discrimination result.

In some embodiments, the discrimination model (i.e., the reference model) may include a single discrimination model. The processing device 140 may simultaneously input the predicted imaging signals and the predicted interference signals into the discrimination model, and the discrimination model may simultaneously output a discrimination result of the predicted imaging signals and a discrimination result of the predicted interference signals. For example, the processing device 140 may input the predicted imaging signals, the pure imaging signals, the predicted interference signals, and the pure interference signals into the discrimination model, and the discrimination model may output the probability that the predicted imaging signals are true and the probability that the predicted interference signals are true. For example, the probability of the predicted imaging signals being true may be 0.8, and the probability of the predicted interference signals being true may be 0.8.

In 508, the processing device 140 (e.g., the training module 240) may determine the second prediction model by updating the initial prediction model based on the reference output.

In some embodiments, the initial prediction model may be updated by constructing a loss function based on the reference output, and adjusting parameters of the initial prediction model by optimizing the value of the loss function.

For example, the processing device 140 may respectively construct loss functions based on the first discrimination result and the second discrimination result.

For instance, a first loss function constructed based on the first discrimination result may be represented according to Equation (1):

$$L_1 = -\frac{1}{N}\sum\nolimits_{i=1}^{N}(y_i * \log x_i + (1-y_i) * \log(1-x_i)), \tag{1}$$

where $L_1$ refers to the first loss function; i refers to a serial number of a training sample; $x_i$ refers to a first discrimination result of the input signals of an i-th training sample; $y_i$ refers to a ground truth discrimination result of the input signals of the i-th training sample; and N refers to the number of training samples. For example, the input signals of a training sample may include pure imaging signals or predicted/synthesized imaging signals, the first discrimination result may include a probability that the input signals are true, the ground truth discrimination result of the pure imaging signals may be denoted as 1, and the ground truth discrimination result of the predicted/synthesized imaging signals may be denoted as 0.

A second loss function constructed based on the second discrimination result may be represented according to Equation (2):

$$L_2 = -\frac{1}{N}\sum\nolimits_{i=1}^{N}(y_i * \log x_i + (1-y_i) * \log(1-x_i)), \tag{2}$$

where $L_2$ refers to the second loss function; i refers to a serial number of a training sample; $x_i$ refers to a second discrimination result of the input signals of an i-th training sample; $y_i$ refers to a ground truth discrimination result of the input signals of the i-th training sample; and N refers to the number of the training samples. For example, the input signals of a training sample may include pure interference signals or predicted/synthesized interference signals, the second discrimination result may include a probability that the input signals are true, the ground truth discrimination result of the pure interference signals may be denoted as 1, and the ground truth discrimination result of the predicted/synthesized interference signals may be denoted as 0.

In some embodiments, when the reference model is a signal adversarial network, a third loss function constructed based on the first discrimination result and the second discrimination result may be represented according to Equation (3):

$$L_3 = -\frac{1}{N}\sum\nolimits_{i=1}^{N}(y_i * \log x_i + (1-y_i) * \log(1-x_i)), \tag{2}$$

where $L_3$ refers to the third loss function; i refers to a serial number of a training sample; $x_i$ refers to a discrimination result of the input signals of an i-th training sample; $y_i$ refers to a ground truth discrimination result of the i-th training sample; and N refers to the number of the training samples. For example, the input signals of a training sample may include pure imaging signals, pure interference signals, predicted/synthesized imaging signals, or predicted/synthesized interference signals, the discrimination result may include a probability that the input signals are true, the ground truth discrimination result of the pure imaging signals may be denoted as 1, the ground truth discrimination result of the predicted/synthesized imaging signals may be denoted as 0, the ground truth discrimination result of the pure interference signals may be denoted as 1, and the ground truth discrimination result of the predicted/synthesized interference signals may be denoted as 0.

By setting the discrimination model as a separate first discrimination model and a separate second discrimination model, the first discrimination model and the second discrimination model can be trained alternately, and can improve the training effect of the models.

In some embodiments, the processing device 140 may train the second prediction model through a signal fusion model based on a relationship between signal separation and signal fusion. The relationship between signal separation and signal fusion is that after an initial signal is separated into two signals, a fused signal obtained by fusing the two signals should be equal to the initial signal. However, in practice, after the initial signal is input into the second prediction model, the second prediction model outputs a predicted imaging signal and a predicted interference signal. A signal obtained by performing a simple fusion operation (e.g., a direct addition) on the predicted imaging signal and the predicted interference signal is not necessarily equal to the initial signal. Therefore, by training the signal fusion model to fuse the predicted imaging signal and the predicted interference signal output by the second prediction model, the relationship between signal separation and signal fusion can be learned, the reference model and the initial prediction model can be jointly updated.

Merely by way of example, the reference model may include a signal fusion model and a third discrimination model. Exemplary signal fusion models may include a convolutional neural network (CNN), a recurrent neural network (RNN), or the like, or any combination thereof. The processing device 140 may generate a signal fusion result by processing the predicted imaging signals and the predicted interference signals using the signal fusion model. Correspondingly, the processing device 140 may input the signal fusion result and the sample initial signals into the third discrimination model to determine the reference output. The reference output may include a third discrimination result relating to the signal fusion result and the sample initial signals. For example, the third discrimination result output by the third discrimination model may include a determination result of whether the signal fusion result is real, a probability that the signal fusion result is real, etc. The processing device 140 may determine the second prediction model by jointly updating the signal fusion model and the initial prediction model based on the reference output.

In some embodiments, the processing device 140 may construct a loss function (e.g., a fourth loss function) based on the signal fusion result, and adjust parameters of the initial prediction model by optimizing the value of the loss function.

For instance, the fourth loss function constructed based on the signal fusion result and the initial signal may be represented according to Equation (4):

$$L_4 = -\frac{1}{N}\sum_i (s_i - s_i')^2, \tag{4}$$

where $L_4$ refers to the fourth loss function; i refers to a serial number of a training sample; $s_i$ refers to the sample initial signals of an i-th training sample; $s_i'$; refers to a signal fusion result of the i-th training sample; and N refers to the total number of the training samples.

In some embodiments, the processing device 140 may train the second predication model based on the adversarial learning algorithm. Alternatively, the processing device 140 may train the second predication model based on signal fusion. The processing device 140 may also train the second predication model based on the adversarial learning algorithm and signal fusion. For example, the processing device 140 may simultaneously use the predicted imaging signals and the predicted interference signals as the output of the discrimination model and the signal fusion model, and construct a loss function based on the outputs of the discrimination model and the signal fusion model to train the second predication model. For example, the constructed loss function may be $L=L_3+L_4$.

In some embodiments, the processing device 140 may alternately optimize each of the above loss functions (e.g., the first loss function, the second loss function, and the fourth loss function) step by step. Alternatively, the processing device 140 may optimize an overall loss function. In some embodiments, the processing device 140 may also assign a weight to each of the above loss functions. The weights may be determined based on experience. The type and determination manner of the loss functions used in training the second prediction model may not be limited in the present disclosure. For example, a loss function provided above may be modified according to any other common loss functions.

In some embodiments, the discrimination model and/or the signal fusion model may be a pre-trained model. That is, the discrimination model and/or the signal fusion model may be pre-trained using training data before training the second prediction model. For example, the processing device 140 may fix the parameters of the second initial prediction model, and use the predicted imaging signals and/or the predicted interference signals to train the discrimination model, so as to optimize the parameters of the discrimination model. As another example, the processing device 140 may fix the parameters of the second initial prediction model, and use the predicted imaging signals and the predicted interference signals to train the signal fusion model, so as to optimize the parameters of the signal fusion model. In some embodiments, the processing device 140 may alternatively pre-train the discrimination model and/or the signal fusion model.

In some embodiments, the second prediction model may include an imaging signal branch and an interference signal branch. The imaging signal branch may be used to output the predicted imaging signals, and the interference signal branch may be used to output the predicted interference signals. More descriptions regarding the imaging signal branch and the interference signal branch may be found elsewhere in the present disclosure (e.g., FIG. 7 and the descriptions thereof).

According to some embodiments of the present disclosure, the second prediction model can be determined by training the initial prediction model based on the adversarial learning algorithm. Therefore, the complex relationship between the unwanted interference signals and the target imaging signals in the initial signal can be considered, which can improve the accuracy of the target imaging signal prediction. In addition, through the adversarial learning algorithm, the problem that the receiver coil cannot collect the imaging signals without the interference signals or collect the unwanted interference signals without the imaging signals when the signal interference exists and the sample subject is excited can be solved, which can increase the amount of the training data, thereby improving the prediction accuracy of the second prediction model, and further improving the accuracy of the target imaging signal prediction.

In some embodiments, the processing device 140 may generate different second pre-trained prediction models for different types and/or degrees of interference signals. Each of the plurality of second pre-trained prediction models may be generated in a similar manner to how the second prediction model is generated as described in process 500. The processing device 140 may determine the second prediction model from the plurality of second pre-trained prediction models based on feature information of the first interference signals. The second prediction model may be determined in a similar manner to how the first prediction model is generated from a plurality of pre-trained prediction models as described in operation 404. Therefore, the matching degree between the second prediction model and the first interference signals can be improved, which can reduce additional acquisition time/computation for real-time model training, thereby improving the accuracy of the interference signal reduction.

Figure 6:
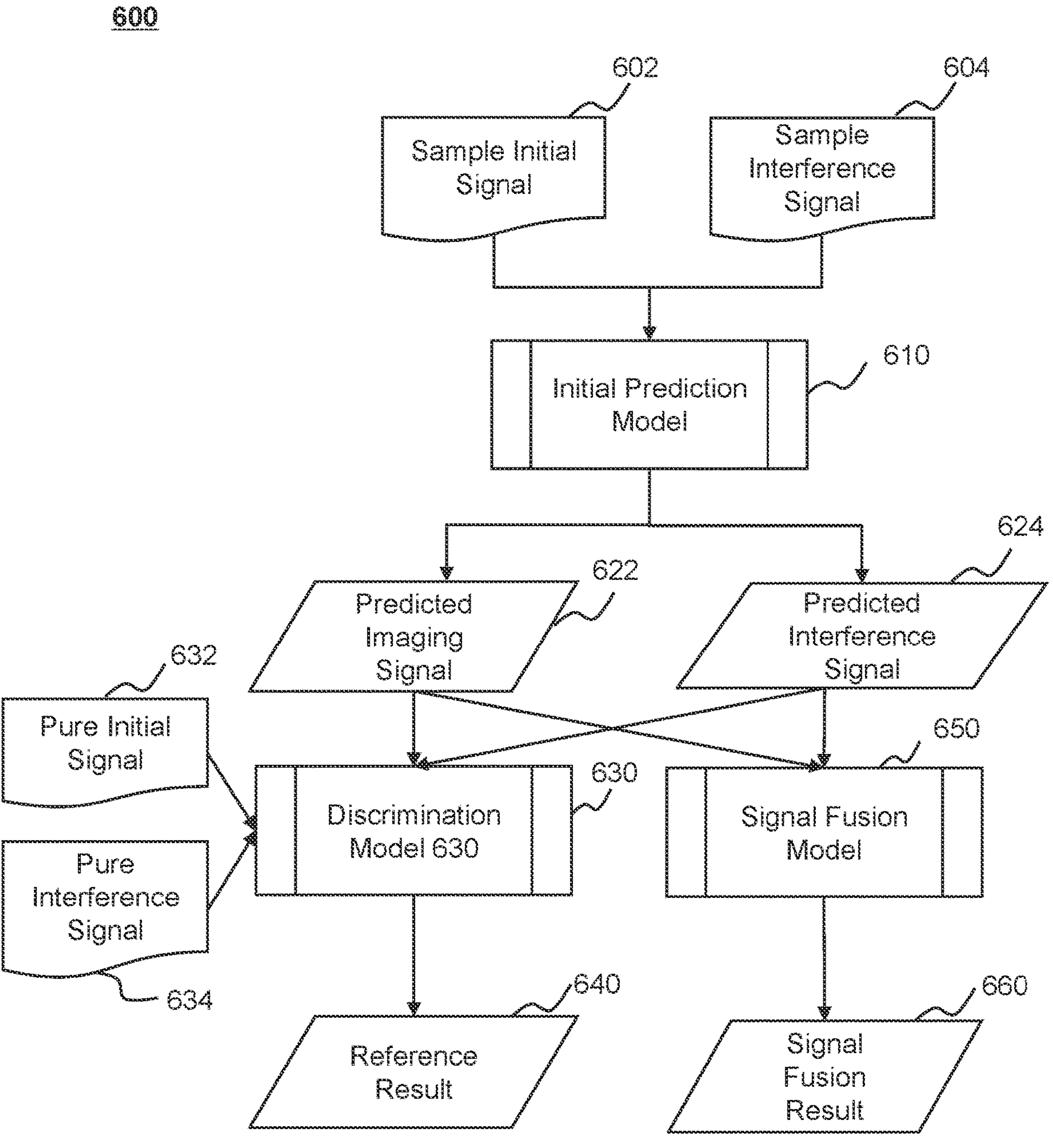
FIG. 6 is a schematic diagram illustrating an exemplary process for determining a second prediction model according to some embodiments of the present disclosure.

FIG. 6 is a schematic diagram illustrating an exemplary process 600 for training a second prediction model according to some embodiments of the present disclosure.

As shown in FIG. 6, in some embodiments, a sample initial signal 602 and a sample interference signal 604 may be input into an initial prediction model (or a second prediction model to be further trained) 610, and the initial prediction model 610 may output a predicted imaging signal 622 and a predicted interference signal 624 by processing the sample initial signal 602 and the sample interference signal 604.

In some embodiments, the predicted imaging signal 622 and the predicted interference signal 624 may be input into a discrimination model 630. At the same time, a pure imaging signal 632 and a pure interference signal 634 may be input into the discrimination model 630. The discrimination model 630 may output a reference output 640 after processing the input data (e.g., the predicted imaging signal 622, the predicted interference signal 624, the pure imaging signal 632, and the pure interference signal 634). The reference output 640 may include, for example, the probability that the predicted imaging signal 622 is real (not generated by the second prediction model), the probability that the predicted interference signal 624 is real, etc.

In some embodiments, the predicted imaging signal 622 and the predicted interference signal 624 may be input into a signal fusion model 650, and the signal fusion model 650 may output a signal fusion result 660 after processing the predicted imaging signal 622 and the predicted interference signal 624. The signal fusion result 660 may include a predicted initial signal generated by fusing the predicted imaging signal 622 and the predicted interference signal 624. In some embodiments, the signal fusion result 660 may be the same as the sample initial signal 602. Alternatively, the signal fusion result 660 may be different from the sample initial signal 602. In some embodiments, parameters of the initial prediction model 610 and/or the signal fusion model 650 may be adjusted based on difference(s) between the signal fusion result 660 and the sample initial signal 602.

In some embodiments, the discrimination model 630 and the signal fusion model 650 may be used separately. For example, when only using the discrimination model 630 the parameters of the initial prediction model 610 may be adjusted based on the reference output 640 of the discrimination model 630. As another example, when only using the signal fusion model 650, the parameters of the initial prediction model 610 may be adjusted based on the signal fusion result 660 of the signal fusion model 650.

In some embodiments, the discrimination model 630 and the signal fusion model 650 may be used simultaneously, for example, the parameters of the initial prediction model 610 may be adjusted based on the reference output 640 of the discrimination model 630 and the signal fusion result 660 of the signal fusion model 650.

Figure 7:
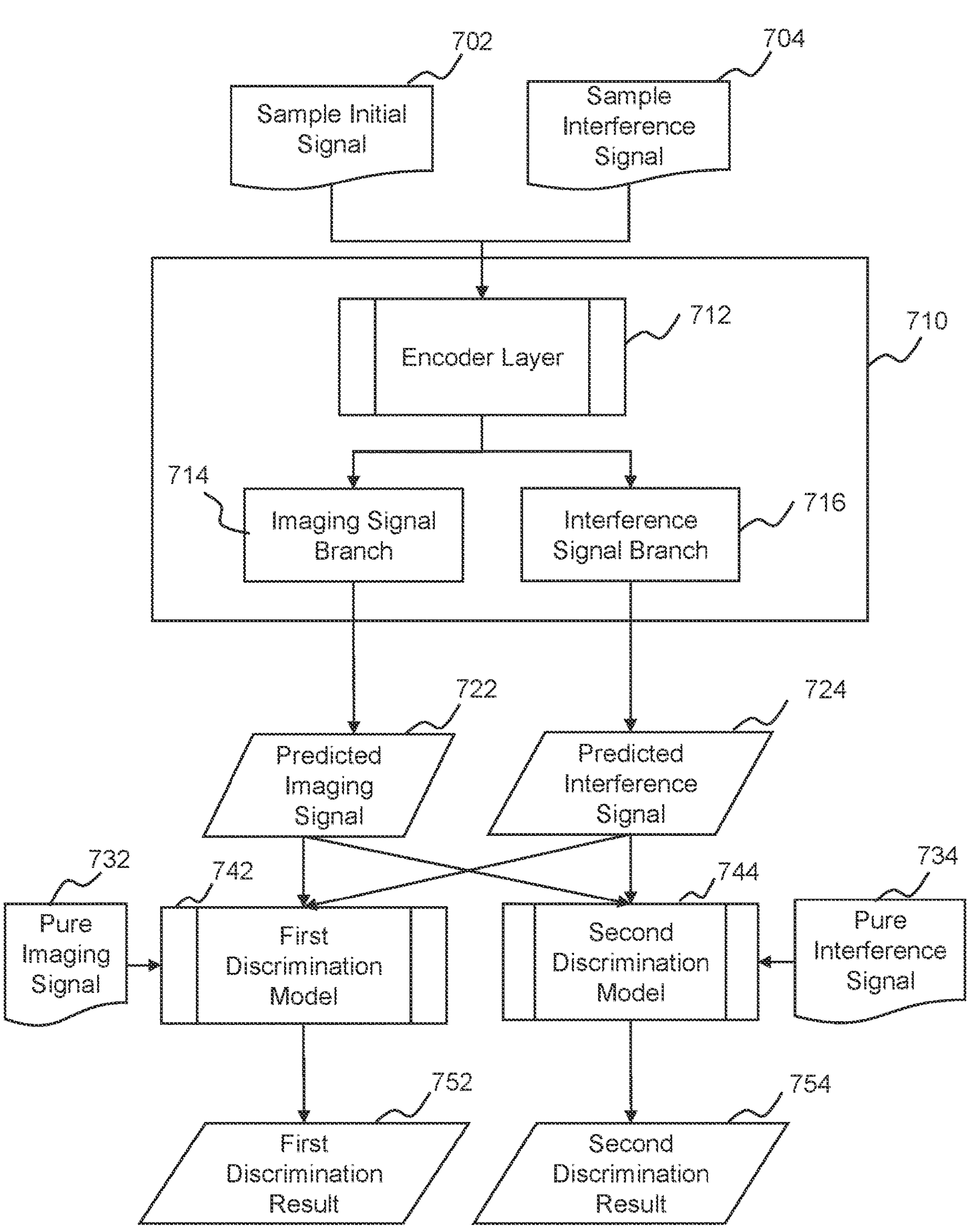
FIG. 7 is a schematic diagram illustrating an exemplary process for determining a second prediction model according to some embodiments of the present disclosure.

FIG. 7 is a schematic diagram illustrating an exemplary process 700 for training a second prediction model according to some embodiments of the present disclosure.

As shown in FIG. 7, in some embodiments, a sample initial signal 702 and a sample interference signal 704 may be input into an initial prediction model (or a second prediction model to be further trained) 710. The sample initial signal 702 and the sample interference signal 704 may be encoded through an encoder layer 712 to generate an encoded result corresponding to the sample initial signal 702 and an encoded result corresponding to the sample interference signal 704, respectively. The encoded result corresponding to the sample initial signal 702 may be input into an imaging signal branch 714, and the encoded result corresponding to the sample interference signal 704 may be input into an interference signal branch 716. The imaging signal branch 714 may output a predicted imaging signal 722 by processing the encoded result corresponding to the sample initial signal 702, and the interference signal branch 716 may output a predicted interference signal 724 by processing the encoded result corresponding to the sample interference signal 704. In some embodiments, the imaging signal branch 714 and the interference signal branch 716 may be decoder layers.

In some embodiments, the predicted imaging signal 722 and a pure imaging signal 732 may be simultaneously input into a first discrimination model 742, and the predicted interference signal 724 and a pure interference signal 734 may be simultaneously input into a second discrimination model 744. The first discrimination model 742 may output a first discrimination result 752 by processing the predicted imaging signal 722 and the pure imaging signal 732, and the second discrimination model 744 may output a second discrimination result 754 by processing the predicted interference signal 724 and the pure interference signal 734.

In some embodiments, the imaging signal branch 714 and the interference signal branch 716 may be pre-trained before the initial prediction model 710 is trained. For example, the imaging signal branch 714 and the interference signal branch 716 may be pre-trained through corresponding discrimination models, respectively. For instance, the imaging signal branch 714 may be pre-trained through a loss function constructed based on the first discrimination result 752 output by the first discrimination model 742, and the interference signal branch 716 may be pre-trained through a loss function constructed based on the second discrimination result 754 output by the second discrimination model 744.

By setting the imaging signal branch 714 and the interference signal branch 716, the encoder layer 712 may be trained using two kinds of data, respectively. For example, the encoder layer 712, the imaging signal branch 714, and the first discrimination model 742 may be trained using the pure imaging signal 732, the sample initial signal 702, and the sample interference signal 704. As another example, the encoder layer 712, the interference signal branch 716, and the second discrimination model 744 may be trained using the pure interference signal 734, the sample initial signal 702, and the sample interference signal 704. Therefore, the flexibility of the model training and the training effect of the models can be improved. At the same time, the flexibility of the model usage can be improved. For example, interference signals can be corrected by using the encoder layer 712 and the imaging signal branch 714, thereby improving the efficiency of the MR image generation.

Figure 8:
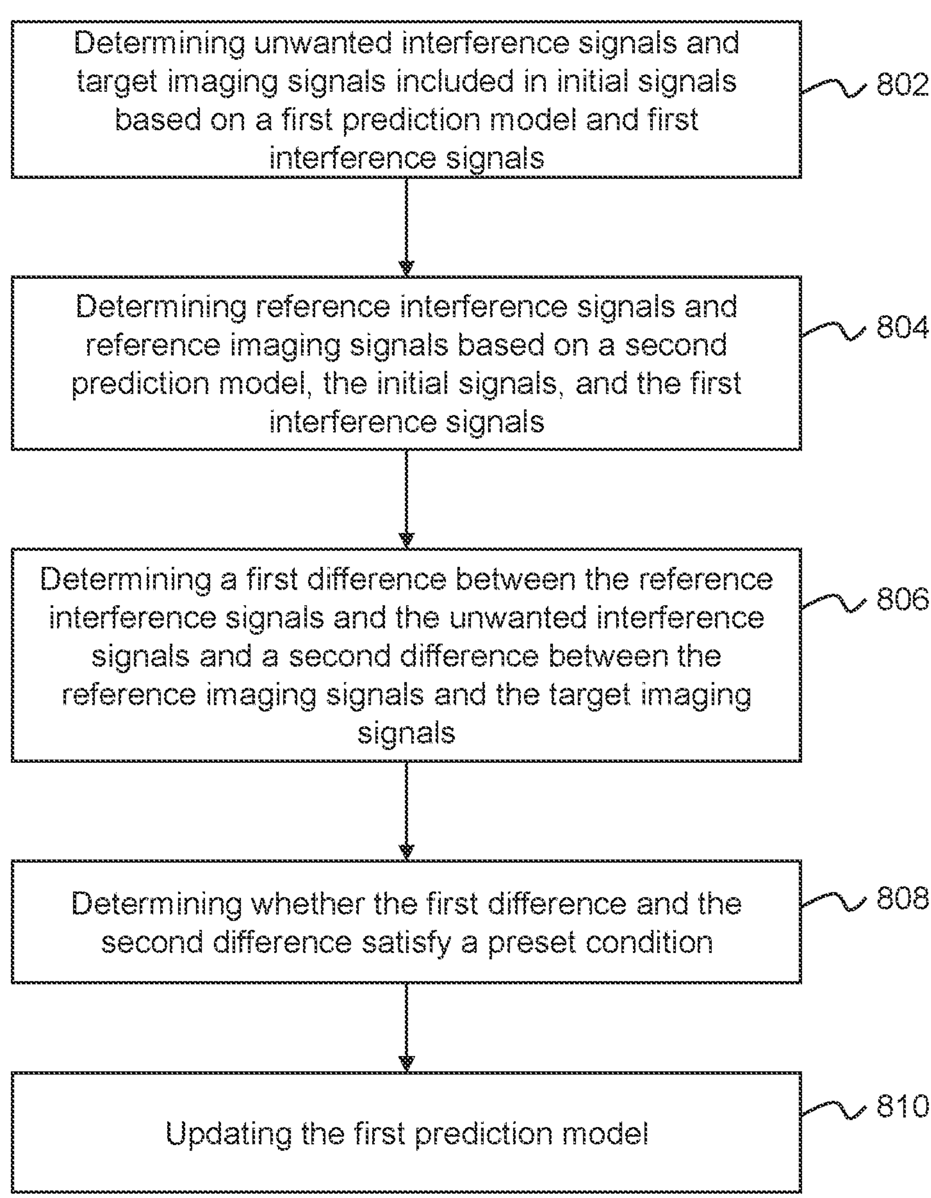
FIG. 8 is a flowchart illustrating an exemplary process for updating a first prediction model according to some embodiments of the present disclosure.

FIG. 8 is a flowchart illustrating an exemplary process 800 for updating a first prediction model according to some embodiments of the present disclosure. In some embodiments, the process 800 may be performed to achieve at least part of operation 404 as described in connection with FIG. 4A.

In 802, the processing device 140 (e.g., the determination module 220) may determine unwanted interference signals and target imaging signals included in initial signals based on a first prediction model and first interference signals.

Figure 4B:
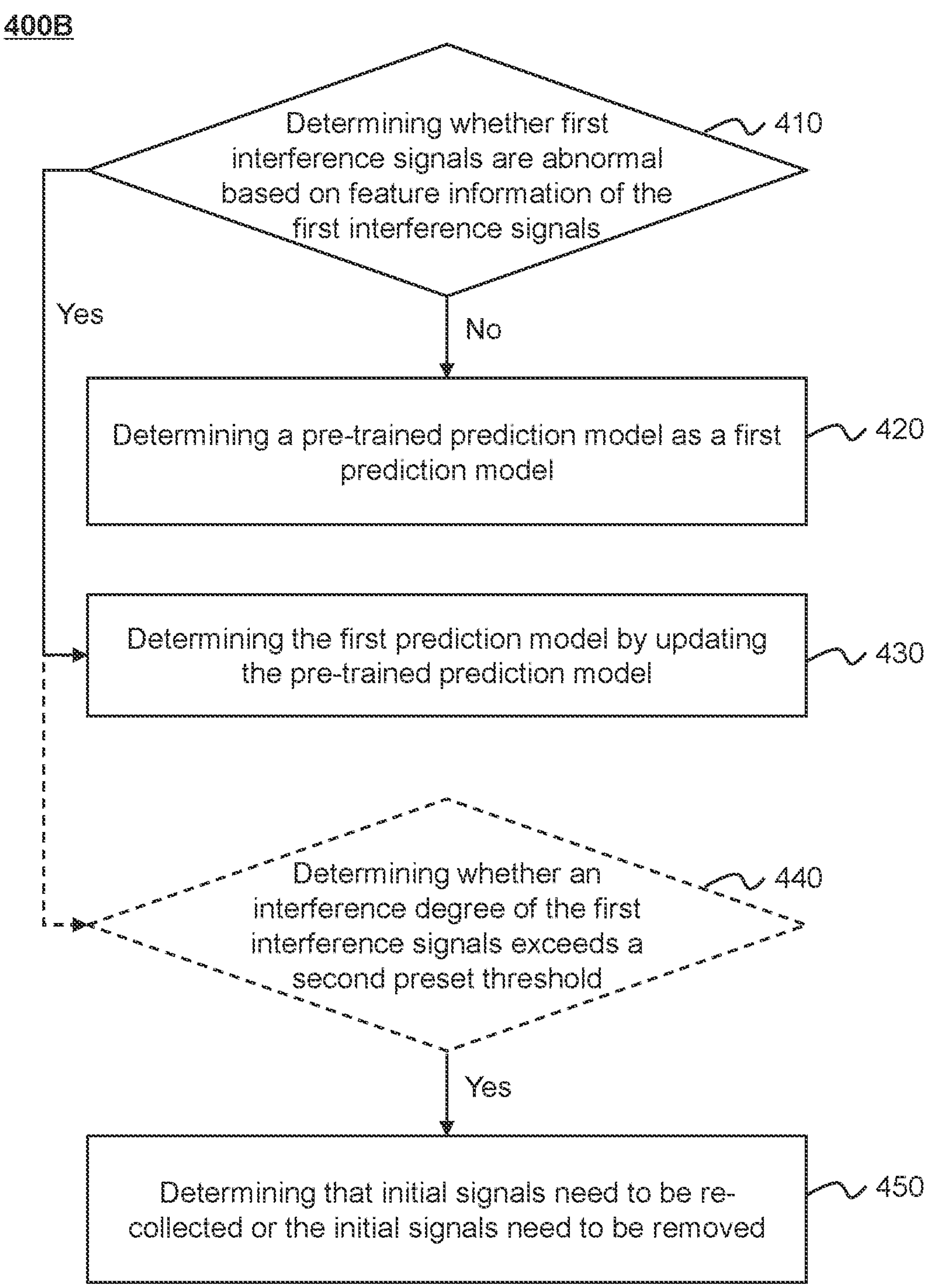
FIG. 4B is a flowchart illustrating an exemplary process for determining a first prediction model according to some embodiments of the present disclosure.

For example, the processing device 140 may input the first interference signals (and the initial signals) into the first prediction model, and the first prediction model may output the unwanted interference signals included in the initial signals. More descriptions regarding the determination of unwanted interference signals may be found elsewhere in the present disclosure (e.g., FIGS. 3 and 4, and the descriptions thereof).

In 804, the processing device 140 (e.g., the determination module 220) may determine reference interference signals and reference imaging signals based on a second prediction model, the initial signals, and the first interference signals.

The reference interference signals may refer to interference signals obtained by processing the first interference signals and the initial signals using the second prediction model.

The reference imaging signals may refer to imaging signals obtained by processing the first interference signals and the initial signals using the second prediction model.

In some embodiments, the reference interference signals may be an interference signal component in the initial signals predicted by the second prediction model, and the reference imaging signals may be an imaging signal component in the initial signals predicted by the second prediction model.

In some embodiments, the processing device 140 may input the first interference signal and the initial signals into the second prediction model, and the second prediction model may output the reference interference signals and the reference imaging signals.

In 806, the processing device 140 (e.g., the determination module 220) may determine a first difference between the reference interference signals and the unwanted interference signals and a second difference between the reference imaging signals and the target imaging signals.

In some embodiments, the processing device 140 may determine the first difference and/or the second difference through a subtraction operation. For example, the processing device 140 may determine the first difference by subtracting the reference interference signals from the unwanted interference signals. Alternatively, the processing device 140 may determine the first difference by subtracting the unwanted interference signals from the reference interference signals. As another example, the processing device 140 may determine the second difference by subtracting the imaging interference signals from the target imaging signals. Alternatively, the processing device 140 may determine the second difference by subtracting the target imaging signals from the reference imaging signals.

In some embodiments, the processing device 140 may determine an absolute value of a difference between the reference interference signals and the unwanted interference signals as the first difference, and determine an absolute value of a difference between the reference imaging signals and the target imaging signals as the second difference.

In 808, the processing device 140 (e.g., the determination module 220) may determine whether the first difference and the second difference satisfy a preset condition.

The preset condition may refer to that the first difference exceeds a first difference threshold and/or the second difference exceeds a second difference threshold. The first difference threshold and/or the second difference threshold may be set as 1, 2, 5, 20, 50, etc. The first difference threshold and/or the second difference threshold may be manually set based on experience or in other manners, which is not limited herein.

In some embodiments, the first difference threshold may be the same as the second difference threshold. Alternatively, the first difference threshold may be different from the second difference threshold.

If the preset condition is satisfied, the process 800 may proceed to operation 810.

In 810, the processing device 140 (e.g., the determination module 220) may update the first prediction model.

In some embodiments, the processing device 140 may update the first prediction model online (e.g., during the MR scan). For example, the processing device 140 may obtain second interference signals and third interference signals collected in a second time window of the MR scan of the target subject when the target subject is in an unexcited state. The second interference signals may be collected by the receiver coil of the MRI device, and the third interference signals may be collected by the interference signal acquisition device. The processing device 140 may update the first prediction model based on the second interference signals and the third interference signals.

According to some embodiments of the present disclosure, by determining whether the first difference and the second difference satisfy the preset condition, whether the first prediction model needs to be updated can be determined based on the first difference and the second difference. When the first difference and the second difference satisfy the preset condition, difference(s) between a prediction result of the first prediction model and a prediction result of the second prediction model are relatively large, which indicates that the first prediction model is not suitable for the first interference signals or the scenario corresponding to the first interference signals and the first prediction model needs to be updated. Correspondingly, the first prediction model can be updated online, which can improve the prediction accuracy of the first prediction model, thereby improving the accuracy of the interference signal prediction.

Figure 9:
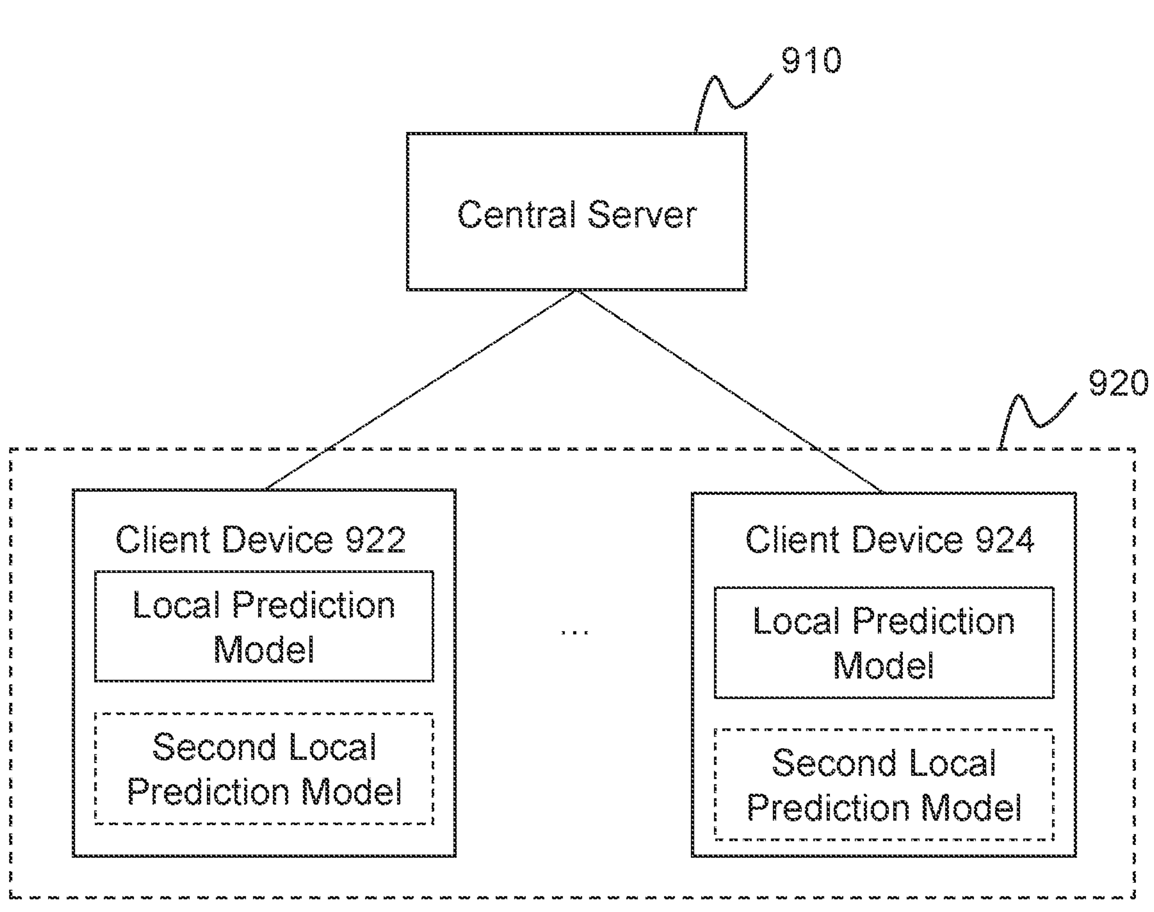
FIG. 9 is a schematic diagram illustrating an exemplary training system according to some embodiments of the present disclosure.

FIG. 9 is a schematic diagram illustrating an exemplary training system 900 according to some embodiments of the present disclosure.

In some embodiments, the effect of unwanted interference signals in initial signals can be reduced through a prediction model (e.g., the first prediction model, the second prediction model, etc.), which reduces requirement(s) for a shielding environment during an MR scan, thereby reducing construction costs and increasing usage scenarios for the MR scan. However, the prediction model is often trained using data pre-collected in certain hospitals or sites. Alternatively, the prediction model is updated or optimized using data collected by an MRI device corresponding to the prediction model. Therefore, the amount of training data is limited, the accuracy of the prediction model may not be accurate enough and need to be improved. In order to increase an amount of training data and improve the reduction effect of the prediction model, the training system 900 is provided.

As illustrated in FIG. 9, the training system 900 may include a federated training system including a central server 910 and client devices 920. The client devices 920 may be a client device 922, a client device 924, etc.

In some embodiments, the central server 910 may be configured to maintain a global prediction model for signal prediction. For example, the central server 910 may include a processing device (e.g., a processor, a server, or a server cluster (which includes multiple micro servers)) used for generating and/or updating the global prediction model, processing information relating to the global prediction model, etc. As another example, the central server 910 may include a storage device (e.g., a mass storage, a removable storage, a volatile read-and-write memory, a read-only memory (ROM), or the like, or any combination thereof) used for storing the global prediction model, the information relating to the global prediction model, etc. Merely by way of example, the central server 910 may be implemented by the processing device 140 of the signal processing system 100.

Each of the client devices 920 (e.g., the client device 922, the client device 924, the client device 926, etc.) may be configured to maintain a local prediction model (also referred to as a first local prediction model) for interference signal prediction corresponding to at least one magnetic resonance imaging (MRI) device. Exemplary local prediction models may include the first prediction model, the second prediction model, or the like, or any combination thereof. As used herein, a local prediction model corresponding to an MRI device refers to that the local prediction model can be used to predict interference signals collected by the MRI device. For example, each local prediction model may correspond to one MRI device, one type of MRI devices, MRI devices of one institution (e.g., one hospital).

In some embodiments, the client devices 920 may be implemented by a plurality of terminals 140 as shown in FIG. 1. For example, the client devices 920 may be computers of different hospitals, and each client device 920 may be used to maintain a local prediction model of the corresponding hospital.

In some embodiments, a type of the global prediction model may be the same as a type of the local prediction models. For example, the global prediction model and the local prediction models may be the first prediction model. In some embodiments, a structure of the global prediction model may be the same as or partially same as a structure of the local prediction models. For example, the global prediction model and the local prediction models may include the same input layer, the same interlayer(s), and the same output layer, but activation functions between the input layer and the output layer are different. As another example, the global prediction model and the local prediction models may include the same input layer, the same interlayer(s), and the same output layer, but cost functions are different. As still another example, the global prediction model and the local prediction models may include the same input layer, the same interlayer(s), and the same output layer, but include different specific partial structures.

In some embodiments, the central server 910 may be communicatively connected with the client devices 920. For example, the central server 910 may be communicatively connected with the client device 922 and the client device 924, respectively, via a wireless connection (e.g., a network), a wired connection, or a combination thereof.

In some embodiments, information and/or data may be transmitted between the central server 910 and the client devices 920. Merely by way of example, the client devices 920 may include one or more target client devices. A target client device refers to a client device that receives new sample data. Each of the one or more target client devices may receive new sample data from the at least one MRI device corresponding to the target client device, generate an updated local prediction model by updating its local prediction model using the new sample data, and transmit first model information relating to the updated local prediction model to the central server 910. The central server 910 may generate an updated global prediction model by updating the global prediction model based on the first model information received from the one or more target client devices, and transmit second model information relating to the updated global prediction model to each of the client devices 920 such that the client devices 920 can update their respective local prediction models based on the second model information. More descriptions regarding the update of the local prediction model and the global prediction model may be found elsewhere in the present disclosure (e.g., FIGS. 10-12 and the descriptions thereof).

In some embodiments, each of the client devices 920 may be further configured to maintain a second local prediction model. The second local prediction model of a client device refers to a prediction model that is updated by the client device and is not used to update the global prediction model. For example, model information relating to the second local prediction model is not transmitted to the central server 910. In some embodiments, a type of the first local prediction model may be the same as or different from a type of the second local prediction models.

It should be noted that the training system 900 is provided for illustration purposes, and is not intended to limit the scope of the present disclosure. For persons having ordinary skills in the art, multiple variations and modifications may be made under the teachings of the present disclosure. However, those variations and modifications do not depart from the scope of the present disclosure.

Figure 10:
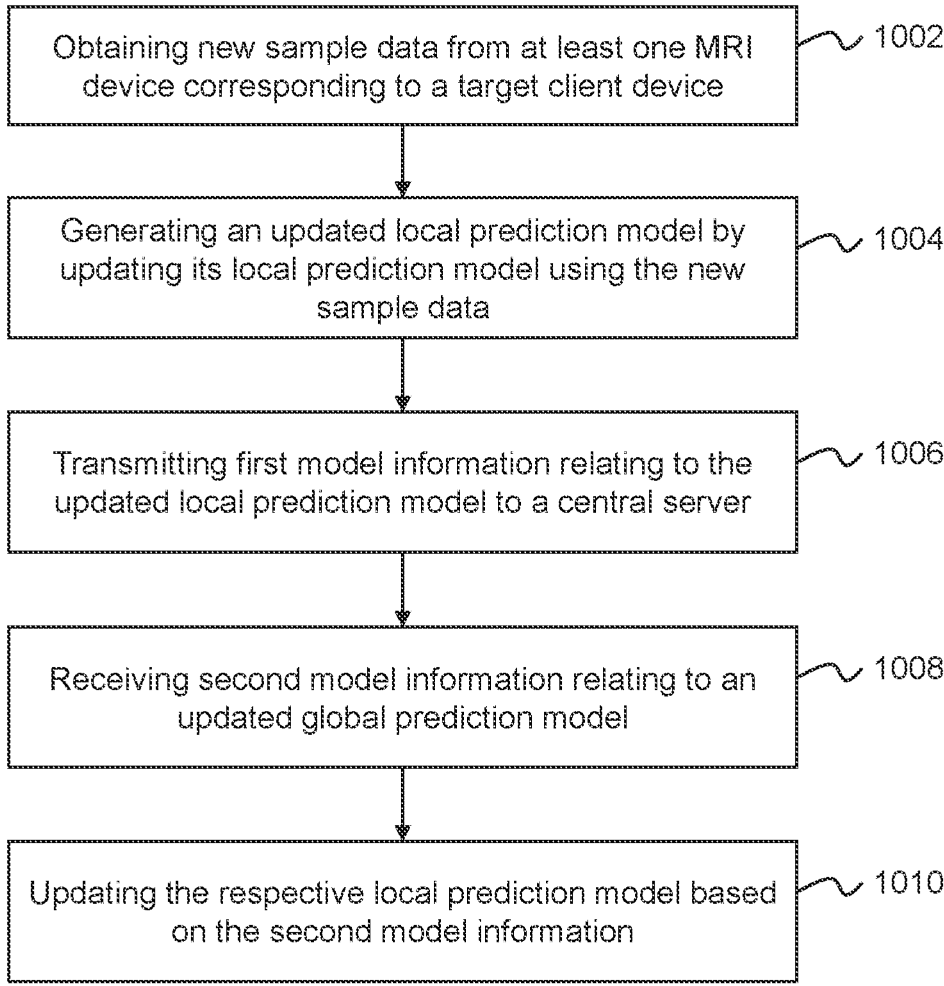
FIG. 10 is a flowchart illustrating an exemplary process for updating a local prediction model according to some embodiments of the present disclosure.

FIG. 10 is a flowchart illustrating an exemplary process 1000 for updating a local prediction model according to some embodiments of the present disclosure.

In some embodiments, the process 1000 may be performed by a target client device (e.g., a processor of the target client device) to update a local prediction model corresponding to at least one MRI device. In some embodiments, one or more client devices of the training system 900 may serve as target client devices, and each of them may perform the process 1000.

In 1002, the target client device may obtain new sample data from at least one MRI device corresponding to the target client device.

The new sample data may refer to sample data that has not been used to train a local prediction model corresponding to the at least one MRI device.

In some embodiments, the new sample data may include first sample interference signals and second sample interference signals. The first sample interference signals may be collected by at least one receiver coil of the at least one MRI device corresponding to the target client device, and the second sample interference signals may be collected by at least one interference signal acquisition device (e.g., the interference signal acquisition device 160) corresponding to the target client device. In some embodiments, if the local prediction model is the first prediction model described above, the first sample interference signals may be collected in a similar manner to how the second interference signals are collected as described in operation 404, and the second sample interference signals may be collected in a similar manner to how the third interference signals are collected as described in operation 404. In some embodiments, if the local prediction model is the second prediction model described above, the new sample data may further include sample initial signals, and the sample initial signals may be obtained in a similar manner as how the initial signals are obtained as described in operation 302. For illustration purposes, the local prediction model being the first prediction model is taken as an example below.

In some embodiments, the new sample data may include signals collected in real time, historical signals collected, signals stored in the corresponding MRI device (e.g., the MRI device 110), signals stored in a storage device (e.g., the storage device 150), etc. For example, each of the at least one MRI device may collect the first sample interference signals and each of the at least one interference signal acquisition device may collect the second sample interference signals at time interval(s) between MR scans. The time interval(s) may include a time period before an MR scan, a time period after an MR scan, a non-acquisition period during an MR scan, or the like, or any combination thereof.

In 1004, the target client device may generate an updated local prediction model by updating its local prediction model using the new sample data.

For example, the second sample interference signals may be determined as a training input, and the first sample interference signals may be determined as a training label. The local prediction model may be updated based on the new sample data in a similar manner to how the first prediction model is generated as described in operation 404.

In some embodiments, the target client device may determine whether the local prediction model of the target client device needs to be trained based on the new sample data. For example, the target client device may generate reference interference signals based on the second sample interference signals in the new sample data and the local prediction model of the target client device, and determine a difference between the reference interference signals and the first sample interference signals in the new sample data. The target client device may further determine whether the difference exceeds a difference threshold. If the difference exceeds the difference threshold, the target client device may determine that the local prediction model of the target client device needs to be trained. More descriptions regarding the determination of whether the local prediction model needs to be trained may be found elsewhere in the present disclosure (e.g., FIGS. 4 and 8, and the descriptions thereof).

If the local prediction model of the target client device needs to be trained based on the new sample data, the target client device may generate the updated local prediction model by updating its local prediction model using the new sample data. If the local prediction model of the target client device does not need to be trained based on the new sample data, the target client device may end the process 1000. In other words, when the prediction effect of the local prediction model with respect to the new sample data satisfies user requirements (e.g., the prediction accuracy exceeds an accuracy threshold, such as 0.7, 0.8, 0.9, 0.95, etc.), the local prediction model does not need to be trained, which can reduce computation resources and improve the training efficiency. The prediction effect of the local prediction model can be determined based on the difference between the reference interference signals and the first sample interference signals. For example, the prediction effect of the local prediction model may be inversely proportional to the difference. That is, the larger the difference, the less the prediction effect of the local prediction model. In some embodiments, a training frequency may be determined based on the prediction effect of the local prediction model. For example, only when the prediction effect of the local prediction model reduces (e.g., the prediction accuracy does not exceed the accuracy threshold), the model training may be performed. In some embodiments, the training frequency may be determined automatically or set manually by the user. For example, a training frequency may be set to every day, two days, three days, every week, every month, etc.

In some embodiments, the target client device may further include a second local prediction model. The second local prediction model may refer to a prediction model that is updated on the target client device and is not used to update the global prediction model. For example, model information relating to the second local prediction model is not transmitted to the central server.

In some embodiments, the second local prediction model may be trained when the target client device obtains the new sample data. That is, no matter the local prediction model of the target client device needs to be trained based on the new sample data or does not need to be trained based on the new sample data, the target client device may generate an updated second local prediction model by updating the second local prediction model using the new sample data. The second local prediction model may be updated in a similar manner to how the local prediction model is updated.

In some embodiments, the new sample data may include a first portion of the new sample data and a second portion of the new sample data. The first portion of the new sample data may relate to general information of the at least one MRI device corresponding to the target client device, and the second portion of the new sample data may relate to special information of the at least one MRI device corresponding to the target client device. For example, the general information may include general signal interference, such as, signal interference relating to the MRI device 110, signal interference relating to common devices (e.g., a mobile phone, a computer, metals, RF device, etc.), etc. The special information may include signal interference relating to a location where the target client device is located, signal interference relating to a special device, etc. Correspondingly, the local prediction model may be trained using the first portion of the new sample data, and the second local prediction model may be trained using the second portion of the new sample data. Alternatively, the second local prediction model may be trained using the new sample data (e.g., the first portion and the second portion of the new sample data).

At this time, the local prediction model may determine a first component of target signals relating to the general information, and the second local prediction model may determine a second component of the target signals relating to the special information. For example, the local prediction model and the second local prediction model may be similar to the first prediction model. The local prediction model may determine a first component of unwanted interference signals, and the second local prediction model may determine a second component of the unwanted interference signals. The unwanted interference signals may be generated by superposing the first component and the second component of the unwanted interference signals. As another example, the local prediction model and the second local prediction model may be similar to the second prediction model. The local prediction model may determine a first component of target imaging signals, and the second local prediction model may determine a second component of the target imaging signals. The target imaging signals may be generated by superposing the first component and the second component of the target imaging signals.

By introducing the second local prediction model, the special information of the at least one MRI device can be considered, which can improve the adaptation of the local prediction model for different environments, thereby improving the prediction accuracy and robustness of the local prediction model and the accuracy of the signal prediction. In addition, influence of the special information of the at least one MRI device on the global prediction model and other local prediction models corresponding to other client devices can be reduced or eliminated, which further improves the prediction accuracy of the local prediction model.

In 1006, the target client device may transmit first model information relating to the updated local prediction model to a central server.

The first model information may include model parameters, model gradient information, etc., of the updated local prediction model. Exemplary model parameters may include the weight, bias, accuracy, etc., of the updated local prediction model. The model gradient information may indicate a difference between predicted interference signals generated by the local prediction model and the second sample interference signals collected by the at least one interference signal acquisition device (e.g., the interference signal acquisition device 160).

In some embodiments, the target client device may transmit a target portion of the first model information to the central server (e.g., the central server 910). The target portion of the first model information may refer to a portion of the first model information that is different from corresponding model information relating to the local prediction model before being updated. For example, the target client device may determine the target portion of the first model information by comparing the first model information relating to the updated local prediction model and the model information relating to the local prediction model, and transmit the target portion of the first model information relating to the updated local prediction model to the central server.

In some embodiments, the target client device may encrypt the first model information before the transmission of the first model information. For example, the target client device may generate encrypted first model information by encrypting the first model information according to an encrypting rule and/or an encrypting algorithm, and transmit the encrypted first model information to the central server 910. By encrypting the first model information, the transmission safety of the first model information can be improved, which can protect the privacy of the target subject, thereby improving the user experience.

In 1008, the target client device may receive second model information relating to an updated global prediction model.

The second model information may include model parameters, model gradient information, etc., of the updated global prediction model. In some embodiments, the client device may generate the updated global prediction model by updating the global prediction model based on the first model information (or the target portion of the first model information) received from the target client device and/or optionally first model information received from other target client device(s). The target client device may receive the second model information relating to the updated global prediction model from the central server. For example, the target client device may receive encrypted second model information from the central server 910, and obtain the second model information by decrypting the encrypted second model information.

In 1010, the target client device may update the updated local prediction model based on the second model information.

For example, the target client device may update the local prediction model by adjusting the first model information based on the second model information. In some embodiments, the model parameters (or a portion thereof) of the updated local prediction model may be adjusted to be the same as the model parameters (or a portion thereof) of the updated global prediction model. In other words, the client device may adjust its local prediction model so that the adjusted local prediction model is the same as or similar to the updated global prediction model.

It should be noted that, the second model information is transmitted to each of the client devices in the training system, and the local prediction model corresponding to each of the client devices in the training system is updated based on the second model information.

According to some embodiments of the present disclosure, by using a federated training system, data from the client devices can be collected to update the local prediction models corresponding to the client devices and the global prediction model corresponding to the central server without sharing the data. In addition, since the data integrates from the client devices, the universality and accuracy of the updated models can be improved. In addition, only model information (e.g., the first model information, the second model information, etc.) is transmitted between the central server and the client devices, which can avoid the leak of original data (e.g., the new sample data) of subjects, thereby improving the data safety and the user experience.

Figure 11:
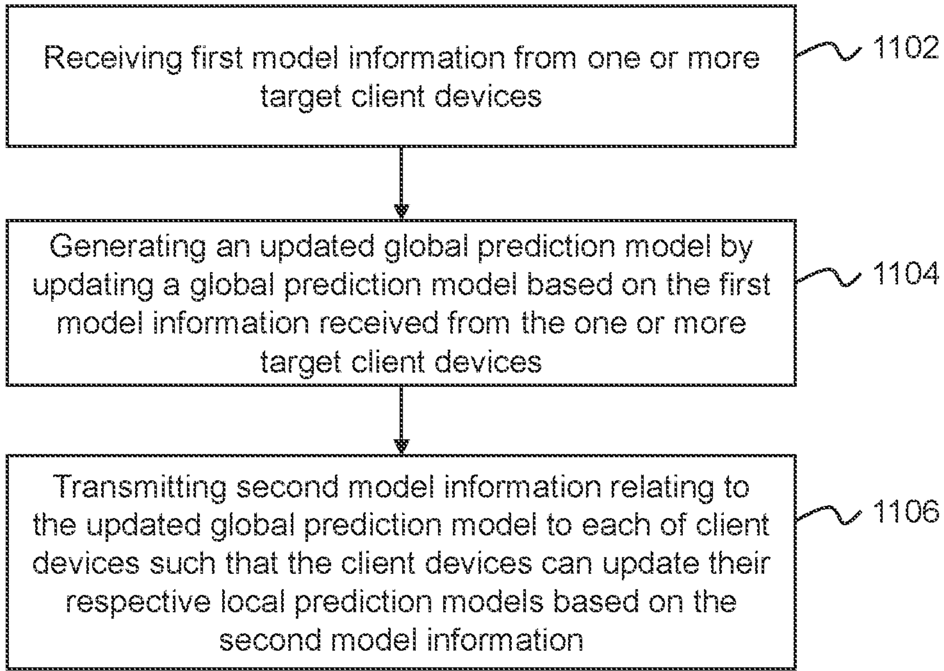
FIG. 11 is a flowchart illustrating an exemplary process for updating a global prediction model according to some embodiments of the present disclosure

FIG. 11 is a flowchart illustrating an exemplary process 1100 for updating a global prediction model according to some embodiments of the present disclosure. In some embodiments, the process 1100 may be performed by a central server (e.g., the central server 910 of the training system 900).

In 1102, the central server 910 may receive first model information from one or more target client devices.

For example, the central server 910 may receive encrypted first model information from the one or more target client devices, and obtain the first model information by decrypting the encrypted first model information.

In 1104, the central server 910 may generate an updated global prediction model by updating a global prediction model based on the first model information received from the one or more target client devices.

For example, the central server 910 may update model parameters of the global prediction model based on the first model information.

In some embodiments, the one or more target client devices may include one client device. Correspondingly, the central server 910 may receive a set of first model information, and update the global prediction model based on the set of first model information.

In some embodiments, the one or more target client devices may include a plurality of target client devices. Correspondingly, the central server 910 may receive a plurality of sets of first model information. In some embodiments, the central server 910 may per-process the plurality of sets of first model information. For example, the central server 910 may determine mean first model information by performing a mean operation on the plurality of sets of first model information. As another example, the central server 910 may determine a weighting value of each target client device and determine weighted first model information by performing a weighting operation on the plurality of sets of first model information based on the weighting values of the target client devices. The weighting value of a target client device may relate to a degree of influence of the set of the first model information received from the target client device on the global prediction model.

Merely by way of example, for each of the plurality of target client devices, the central server 910 may obtain a training condition of the local prediction model of the target client device. The training condition may include a volume of the new sample data used in training the local prediction model, a prediction accuracy of the local prediction model, or the like, or any combination thereof. For each target client device, the central server 910 may determine the weighting value of the target client device based on the training condition of the target client device. For instance, the weighting value may be positively correlated with the volume of the new sample data and/or the prediction accuracy of the new sample data. In some embodiments, the weighting value may be determined based on medical experience or other manners, which is not limited herein.

Merely by way of example, the central server 910 is connected to the client device 922 and the client device 924. When one of the client device 922 and the client device 924 is the target client device, the updated global prediction model may be generated by updating the global prediction model based on first model information received from the target client device. When the client device 922 and the client device 924 are both target client devices, the central server 910 may obtain a first weighting value corresponding to the client device 922 and a second weighting value corresponding to the client device 924, and update the global prediction model based on the first model information received from the client device 922 and the client device 924 the target client device, a first weighting value, and the second weighting value. For instance, if a volume of the new sample data corresponding to the client device 922 is 100, and a volume of the new sample data corresponding to the client device 924 is 200, the first weighting value may be 0.33 and the second weighting value may be 0.67. As another example, if a prediction accuracy of the local prediction model corresponding to the client device 922 is 0.9, and a prediction accuracy of the local prediction model corresponding to the client device 924 is 0.7, the first weighting value may be 0.67 and the second weighting value may be 0.33. As still another example, if the training condition includes the volume of the new sample data and the prediction accuracy of the local prediction model, the central server 910 may further determine a first impact factor of the volume of the new sample data and a second impact factor of the prediction accuracy of the local prediction model. The central server 910 may then determine the first weighting value and the second weighting value based on the first impact factor, the second impact factor, the volume of the new sample data, and the prediction accuracy of the local prediction models.

By introducing the weighting value of each of the plurality of target client devices, the degree of influence of each set of the first model information can be considered, which can improve the prediction accuracy of the global prediction model.

In 1106, the central server 910 may transmit second model information relating to the updated global prediction model to each of client devices such that the client devices can update their respective local prediction models based on the second model information.

In some embodiments, the central server 910 may transmit a target portion of the second model information to each of the client devices (e.g., the client devices 920). The target portion of the second model information may refer to a portion of the second model information that is different from corresponding model information relating to the global prediction model before being updated.

In some embodiments, the processing device 140 may encrypt the second model information before the transmission of the second model information. For example, the processing device 140 may generate encrypted second model information by encrypting the second model information according to an encrypting rule and/or an encrypting algorithm, and transmit the encrypted second model information to the client devices 920. The encrypting rule and/or the encrypting algorithm used on the second model information may be the same as or different from the encrypting rule and/or the encrypting algorithm used on the first model information.

According to some embodiments of the present disclosure, the global prediction model can be updated based on the first model information received from the one or more target client devices, and the second model information can be transmitted to each of the client devices for updating their respective local prediction models based on the second model information. Therefore, based on the new sample data of the one or more target client devices, the global prediction model and the local prediction models in the training system can be jointly updated, which is equivalent to increasing the amount of training data of the global prediction model, thereby improving the accuracy of the global prediction model and the local prediction models.

Figure 12:
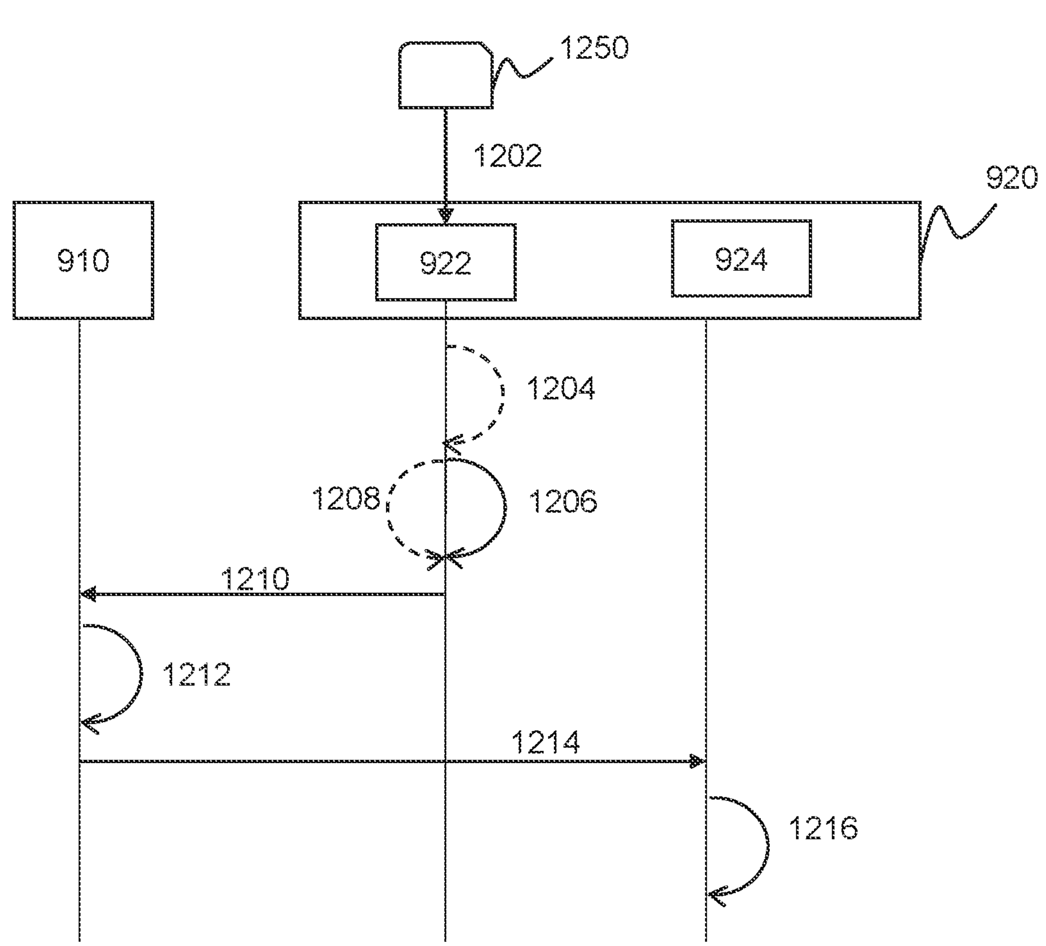
FIG. 12 is a schematic diagram illustrating an exemplary process for model training according to some embodiments of the present disclosure.

FIG. 12 is a schematic diagram illustrating an exemplary process 1200 for model training according to some embodiments of the present disclosure.

In 1202, at least one target client device 922 may receive new sample data 1250 from at least one MRI device corresponding to the target client device 922.

In 1204, the at least one target client device 922 may determine whether a local prediction model corresponding to the at least one target client device 922 needs to be updated based on the new sample data 1250.

In 1206, if the local prediction model corresponding to the at least one target client device 922 needs to be updated based on the new sample data, the at least one target client device 922 may generate an updated local prediction model by updating its local prediction model using the new sample data 1250.

In 1208, if the local prediction model corresponding to the at least one target client device 922 does not need to be updated based on the new sample data 1250, the process 1200 may be ended. In some embodiments, if the at least one target client device 922 includes a second local prediction model, the at least one target client device 922 may generate an updated second local prediction model by updating the second local prediction model using the new sample data 1250.

In 1210, the at least one target client device 922 may transmit first model information relating to the updated local prediction model to the central server 910. For example, the at least one target client device 922 may generate encrypted first model information by encrypting the first model information, and transmit the encrypted first model information to the central server 910.

In 1212, the central server 910 may generate an updated global prediction model by updating a global prediction model corresponding to the central server 910 based on the first model information received from the at least one target client device 922.

In 1214, the central server 910 may transmit second model information relating to the updated global prediction model to each of the client devices 920 (including the at least one target client device 922 and at least one non-target client device 924).

In 1216, each of the client devices 920 may update their respective local prediction models based on the second model information.

Processes 300-800 and 1000-1200 may be implemented in the signal processing system 100 illustrated in FIG. 1 or the training system 900. For example, the processes 300-800 and 1000 may be stored in the storage device 150 in the form of instructions (e.g., an application), and invoked and/or executed by the processing device 140. The operations of the illustrated process presented below are intended to be illustrative. In some embodiments, the processes 300-800 and 1000-1200 may be accomplished with one or more additional operations not described, and/or without one or more of the operations discussed. Additionally, the order in which the operations of the processes 300-800 and 1000-1200 as illustrated in FIGS. 3-8 and 10-12 as described below is not intended to be limiting.

Figure 13:
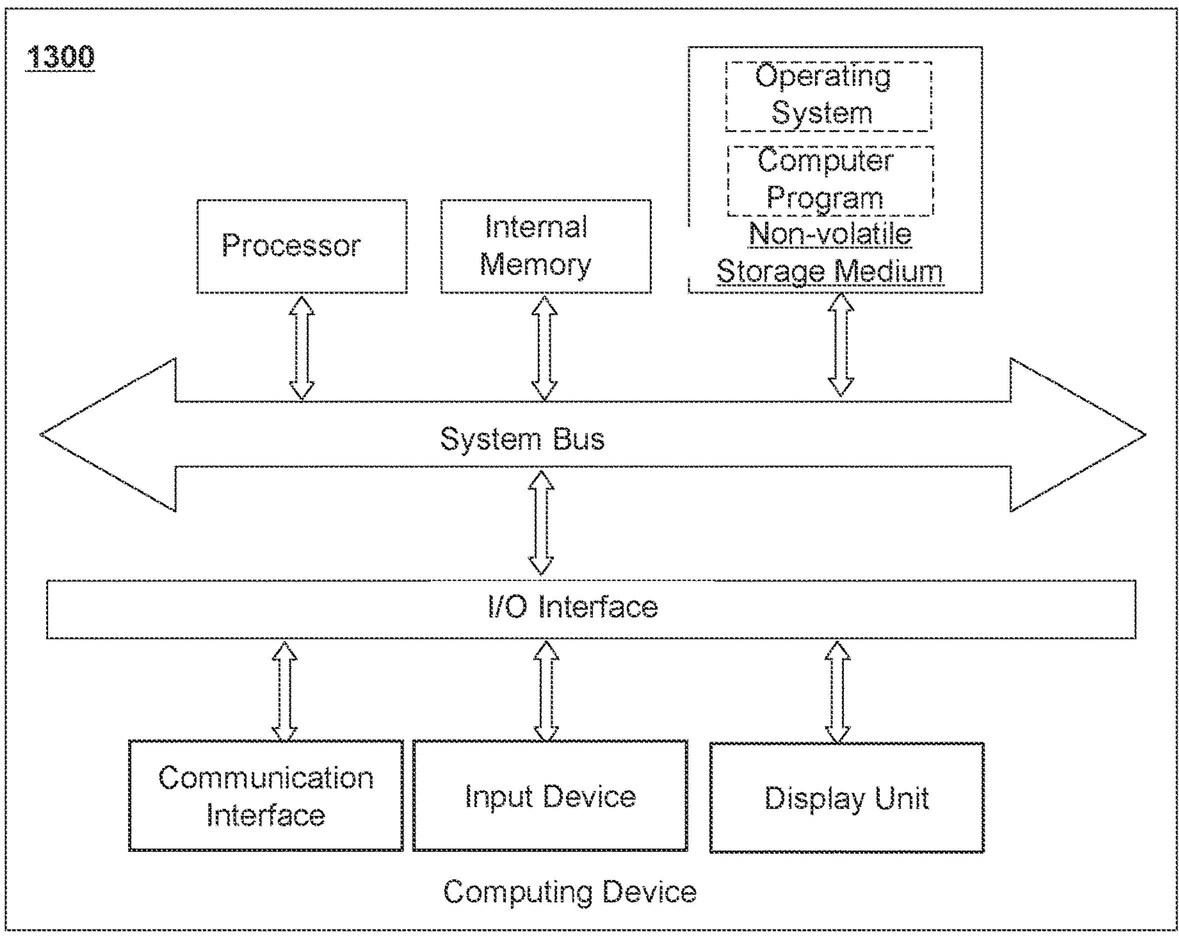
FIG. 13 is a schematic diagram illustrating an exemplary computing device according to some embodiments of the present disclosure.

FIG. 13 is a schematic diagram illustrating an exemplary computing device 1300 according to some embodiments of the present disclosure.

In some embodiments, one or more components of the signal processing system 100 or the training system 900 may be implemented on the computing device 1300. For example, a processing device may be implemented on the computing device 1300 and configured to implement the functions and/or methods disclosed in the present disclosure.

The computing device 1300 may include any components used to implement the signal processing system 100 or the training system 900 described in the present disclosure. For example, the processing device 1300 may be implemented through hardware, software program, firmware, or any combination thereof, on the computing device 1300. For illustration purposes, only one computer is described in FIG. 13, but computing functions related to the signal processing system 100 or the training system 900 described in the present disclosure may be implemented in a distributed fashion by a group of similar platforms to spread the processing load of the signal processing system 100 or the training system 900.

The computing device 1300 may include a communication port connected to a network to achieve data communication. The computing device 1300 may include a processor (e.g., a central processing unit (CPU)), a memory, a communication interface, a display unit, and an input device connected by a system bus. The processor of the computing device 1300 may be used to provide computing and control capabilities. The memory of the computing device 1300 may include a non-volatile storage medium, an internal memory. The non-volatile storage medium may store an operating system and a computer program. The internal memory may provide an environment for the execution of the operating system and the computer program in the non-volatile storage medium. The communication interface of the computing device 1300 may be used for wired or wireless communication with an external terminal. The wireless communication may be realized through Wi-Fi, a mobile cellular network, a near field communication (NFC), etc. When the computer program is executed by the processor, a method for determining feature points may be implemented. The display unit of the computing device 1300 may include a liquid crystal display screen or an electronic ink display screen. The input device of the computing device 1300 may include a touch layer covered on the display unit, a device (e.g., a button, a trackball, a touchpad, etc.) set on the housing of the computing device 1300, an external keyboard, an external trackpad, an external mouse, etc.

Merely for illustration, only one processor is described in FIG. 13. However, it should be noted that the computing device 1300 in the present disclosure may also include multiple processors. Thus operations and/or method steps that are performed by one processor as described in the present disclosure may also be jointly or separately performed by the multiple processors. For example, if the processor of the computing device 1300 in the present disclosure executes both operation A and operation B, it should be understood that operation A and operation B may also be performed by two or more different processors jointly or separately (e.g., a first processor executes operation A and a second processor executes operation B, or the first and second processors jointly execute operations A and B).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:

a central server configured to maintain a global prediction model for signal prediction; and client devices communicatively connected with the central server, wherein:

each of the client devices is configured to maintain a local prediction model for signal prediction corresponding to at least one magnetic resonance imaging (MRI) device, wherein electromagnetic interference (EMI) exists during an MR scan of the at least one MRI device, and the client devices correspond to different hospitals, the client devices include one or more target client devices, each of the one or more target client devices is configured to receive new sample data corresponding to the target client device, generate an updated local prediction model by updating its local prediction model using the new sample data, and transmit first model information relating to the updated local prediction model to the central server, wherein types or degrees of interference signals in the new sample data received by each of the one or more target client devices are different from those in new sample data received by another of the one or more target client devices, and the central server is configured to generate an updated global prediction model by updating the global prediction model based on the first model information received from the one or more target client devices, and transmit second model information relating to the updated global prediction model to each of the client devices such that the client devices can update their respective local prediction models based on the second model information, and an updated local prediction model corresponding to each of the client devices is adapted to a current environment of the at least one MRI device corresponding to the client device.

2. The system of claim 1, wherein for each of the one or more target client devices, the new sample data includes first sample interference signals and second sample interference signals collected during a non-acquisition period in an MR scan or during a time interval between MR scans, the first sample interference signals being collected by at least one receiver coil of the at least one MRI device corresponding to the target client device and used as a training label, and the second sample interference signals being collected by at least one interference signal acquisition device corresponding to the target client device and used as a training input.

3. The system of claim 2, wherein for each target client device, the at least one interference signal acquisition device corresponding to the target client device includes one or more interference signal acquisition coils, and the one or more interference signal acquisition coils are integrated with the at least one MRI device corresponding to the target client device.

4. The system of claim 1, wherein to generate an updated local prediction model by updating its local prediction model using the new sample data, each of the one or more target client devices is further configured to:

determine whether the local prediction model of the target client device needs to be trained based on the new sample data; and in response to determining that the local prediction model of the target client device needs to be trained based on the new sample data, generate the updated local prediction model by updating its local prediction model using the new sample data.

5. The system of claim 4, wherein to determine whether the local prediction model of the target client device needs to be trained based on the new sample data, each of the one or more target client devices is further configured to:

generate reference interference signals based on the second sample interference signals in the new sample data and the local prediction model of the target client device;

determine whether a difference between the reference interference signals and the first sample interference signals in the new sample data exceeds a difference threshold; and in response to determining that the difference exceeds the difference threshold, determine that the local prediction model of the target client device needs to be trained.

6. The system of claim 4, wherein each of the client devices is further configured to maintain a second local prediction model, the second local prediction model is a prediction model that is updated on the corresponding client device but not used to update the global prediction model, and in response to determining that the local prediction model of the target client device does not need to be trained, the target client device is further configured to:

generate an updated second local prediction model by updating the second local prediction model using the new sample data.

7. The system of claim 6, wherein the new sample data includes a first portion of the new sample data and a second portion of the new sample data, the first portion of the new sample data relating to general information of the at least one MRI device corresponding to the target client device, the second portion of the new sample data relating to special information of the at least one MRI device corresponding to the target client device, the local prediction model of the target client device is trained using the first portion of the new sample data, the general information including general signal interference, and the second local prediction model of the client device is trained using the second portion of the new sample data, the special information including at least one of signal interference relating to a location where the target client device is located and signal interference relating to a special device.

8. The system of claim 1, wherein the one or more target client devices include a plurality of target client devices, and to generate an updated global prediction model by updating the global prediction model based on the first model information received from the one or more target client devices, the central server is further configured to:

determine a weighting value corresponding to each of the plurality of target client devices; and generate the updated global prediction model by updating the global prediction model based on the first model information received from the plurality of target client devices and the weighting value corresponding to each of the plurality of target client devices.

9. The system of claim 8, wherein to determine a weighting value corresponding to each of the plurality of target client devices, the central server is further configured to:

for each of the plurality of target client devices, obtain a training condition of the local prediction model of the target client device, the training condition including at least one of a volume of the new sample data used in training the local prediction model and a prediction accuracy of the local prediction model; and determine the weighting value corresponding to each of the plurality of target client devices based on the training condition corresponding to each of the plurality of target client devices.

10. The system of claim 1, wherein each of the client devices is further configured to:

obtain initial signals collected by at least one receiver coil of the at least one MRI device corresponding to the client device;

generate unwanted interference signals based on the updated local prediction model and the initial signals; and determine target imaging signals based on the unwanted interference signals and the initial signals.

11. The system of claim 1, wherein the local prediction model includes a first prediction model for interference signal prediction, and each of the client devices is further configured to:

obtaining initial signals and first interference signals collected in a time window of a medical scan of a target subject when the target subject is in an excited state, the initial signals being collected by a receiver coil of the at least one MRI device corresponding to the client device, and the first interference signals being collected by an interference signal acquisition device corresponding to the client device:

determining feature information of the first interference signals, the feature information including at least one of an interference degree or an interference type:

determining the first prediction model for interference signal prediction from a plurality of pre-trained prediction models based on the feature information of the first interference signals; and determining target imaging signals included in the initial signals based on the first prediction model and the first interference signals.

12. The system of claim 1, wherein the local prediction model includes a second prediction model, and each of the client devices is further configured to:

obtaining initial signals and interference signals collected in a time window of a medical scan of a target subject, the initial signals being collected by a receiver coil of the at least one MRI device corresponding to the client device when the target subject is in an excited state, and the interference signals being collected by an interference signal acquisition device corresponding to the client device;

determining target imaging signals included in the initial signals by processing the initial signals and the interference signals using the second prediction model, the second prediction model being a trained machine learning model; and generating a target MR image of the target subject based on the target imaging signals.

13. A method for signal processing, implemented on a client device among client devices communicatively connected with a central server, wherein the central server is configured to maintain a global prediction model for signal prediction, the client device is configured to maintain a local prediction model for signal prediction corresponding to at least one magnetic resonance imaging (MRI) device, and the method comprises:

obtaining initial signals collected by at least one receiver coil of the at least one MRI device corresponding to the client device;

generating unwanted interference signals based on an updated local prediction model and the initial signals; and determining target imaging signals based on the unwanted interference signals and the initial signals, wherein the updated local prediction model is obtained by:

updating the local prediction models based on second model information from the central server, wherein the client devices include one or more target client devices, each of the one or more target client devices is configured to receive new sample data corresponding to the target client device, generate an updated local prediction model corresponding to the target client device by updating its local prediction model using the new sample data, and transmit first model information relating to the updated local prediction model corresponding to the target client device to the central server, wherein the new sample data includes first sample interference signals and second sample interference signals collected during a non-acquisition period in an MR scan or during a time interval between MR scans, the first sample interference signals are collected by at least one receiver coil of the at least one MRI device corresponding to the target client device and used as a training label, the second sample interference signals are collected by at least one interference signal acquisition device corresponding to the target client device and used as a training input, and the central server is configured to generate an updated global prediction model by updating the global prediction model based on first model information received from the one or more target client devices, and transmit the second model information relating to the updated global prediction model to each of the client devices.

14. The method of claim 13, wherein the generating an updated local prediction model corresponding to the target client device by updating its local prediction model using the new sample data includes:

determining whether the local prediction model of the target client device needs to be trained based on the new sample data; and in response to determining that the local prediction model of the target client device needs to be trained based on the new sample data, generating the updated local prediction model by updating its local prediction model using the new sample data.

15. The method of claim 14, wherein each of the client devices is further configured to maintain a second local prediction model, the second local prediction model is a prediction model that is updated on the corresponding client device but not used to update the global prediction model, and in response to determining that the local prediction model of the target client device does not need to be trained, the method further includes:

generating an updated second local prediction model by updating the second local prediction model using the new sample data.

16. The method of claim 15, wherein the new sample data includes a first portion of the new sample data and a second portion of the new sample data, the first portion of the new sample data relating to general information of the at least one MRI device corresponding to the target client device, the second portion of the new sample data relating to special information of the at least one MRI device corresponding to the target client device, the local prediction model of the target client device is trained using the first portion of the new sample data, the general information including general signal interference, and the second local prediction model of the client device is trained using the second portion of the new sample data, the special information including at least one of signal interference relating to a location where the target client device is located and signal interference relating to a special device.

17. The method of claim 13, wherein the one or more target client devices include a plurality of target client devices, and the generating an updated global prediction model by updating the global prediction model based on first model information received from the one or more target client devices includes:

determining a weighting value corresponding to each of the plurality of target client devices; and generating the updated global prediction model by updating the global prediction model based on the first model information received from the plurality of target client devices and the weighting value corresponding to each of the plurality of target client devices.

18. The method of claim 17, wherein the determining a weighting value corresponding to each of the plurality of target client devices includes:

for each of the plurality of target client devices, obtaining a training condition of the local prediction model of the target client device, the training condition including at least one of a volume of the new sample data used in training the local prediction model and a prediction accuracy of the local prediction model; and determining the weighting value corresponding to each of the plurality of target client devices based on the training condition corresponding to each of the plurality of target client devices.

19. A non-transitory computer readable medium, comprising executable instructions that, when executed by at least one processor, direct the at least one processor to perform a method, the method comprising:

obtaining initial signals collected by at least one receiver coil of at least one medical device corresponding to a client device;

generating unwanted interference signals based on an updated local prediction model and the initial signals; and determining target imaging signals based on the unwanted interference signals and the initial signals, wherein the client device is one of client devices communicatively connected with a central server, the central server is configured to maintain a global prediction model for signal prediction, the client device is configured to maintain a local prediction model for signal prediction corresponding to the at least one medical-magnetic resonance imaging (MRI) device, electromagnetic interference (EMI) exists during an MR scan of the at least one MRI device, and the client devices correspond to different hospitals, and the updated local prediction model is obtained by:

updating the local prediction models based on second model information from the central server, wherein the client devices include one or more target client devices, each of the one or more target client devices is configured to receive new sample data corresponding to the target client device, generate an updated local prediction model corresponding to the target client device by updating its local prediction model using the new sample data, and transmit first model information relating to the updated local prediction model corresponding to the target client device to the central server, wherein types or degrees of interference signals in the new sample data received by each of the one or more target client devices are different from those in new sample data received by another of the one or more target client devices, and the central server is configured to generate an updated global prediction model by updating the global prediction model based on first model information received from the one or more target client devices, and transmit the second model information relating to the updated global prediction model to each of the client devices, and an updated local prediction model corresponding to each of the client devices is adapted to a current environment of the at least one MRI device corresponding to the client device.

20. The system of claim 12, wherein the second prediction model is determined by:

obtaining training data including sample initial signals and sample interference signals, the sample initial signals and the sample interference signals being collected during a sample MR scan of a sample subject when the sample subject is excited;

generating predicted imaging signals and predicted interference signals based on the training data and an initial prediction model;

generating a reference output by processing the predicted imaging signals using a reference model; and determining the second prediction model by updating the initial prediction model based on the reference output.

* * * * *